United States Patent
Smyth

(10) Patent No.: US 12,070,596 B2
(45) Date of Patent: Aug. 27, 2024

(54) PROSTHESIS MANAGEMENT OF BODY PHYSIOLOGY

(71) Applicant: COCHLEAR LIMITED, New South Wales (AU)

(72) Inventor: Daniel Smyth, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 911 days.

(21) Appl. No.: 16/982,713

(22) PCT Filed: Mar. 19, 2019

(86) PCT No.: PCT/IB2019/052225
§ 371 (c)(1),
(2) Date: Sep. 21, 2020

(87) PCT Pub. No.: WO2019/180614
PCT Pub. Date: Sep. 26, 2019

(65) Prior Publication Data
US 2021/0001113 A1    Jan. 7, 2021

Related U.S. Application Data

(60) Provisional application No. 62/645,455, filed on Mar. 20, 2018.

(51) Int. Cl.
*A61N 1/36*    (2006.01)
*A61M 5/172*    (2006.01)
*A61N 1/05*    (2006.01)

(52) U.S. Cl.
CPC ......... *A61N 1/0541* (2013.01); *A61M 5/1723* (2013.01); *A61N 1/36038* (2017.08);
(Continued)

(58) Field of Classification Search
CPC ....... A61B 5/12; A61B 5/4839; A61B 5/6817; A61M 2005/1726; A61M 2205/05;
(Continued)

(56) References Cited

U.S. PATENT DOCUMENTS

| 5,231,580 A | 7/1993 | Cheung et al. |
| 6,266,568 B1 | 7/2001 | Mann et al. |

(Continued)

FOREIGN PATENT DOCUMENTS

| CN | 105451809 A | 3/2016 |
| KR | 20030036118 A | 5/2003 |
| WO | 2015068136 A1 | 5/2015 |

OTHER PUBLICATIONS

Extended European search report for European Patent Application No. 19 772 091.5, mailed Nov. 8, 2021.
(Continued)

*Primary Examiner* — George Manuel
(74) *Attorney, Agent, or Firm* — Pilloff Passino & Cosenza LLP; Martin J. Cosenza

(57) ABSTRACT

An apparatus, such as an implantable medical device, including an implantable device configured to cause trauma in an inner ear and/or a middle ear recipient. In an exemplary embodiment, the implantable device is a cochlear implant. In an exemplary embodiment, the implantable device is configured to deliver a therapeutic substance to body tissue of the recipient.

31 Claims, 19 Drawing Sheets

(52) U.S. Cl.
CPC ............... *A61M 2005/1726* (2013.01); *A61M 2205/054* (2013.01); *A61M 2210/0662* (2013.01)

(58) Field of Classification Search
CPC .... A61M 2205/054; A61M 2210/0662; A61M 5/14276; A61M 5/172; A61M 5/1723; A61N 1/0541; A61N 1/205; A61N 1/36038
See application file for complete search history.

(56) References Cited

U.S. PATENT DOCUMENTS

| | | | |
|---|---|---|---|
| 2005/0171579 A1 | 8/2005 | Tasche et al. | |
| 2008/0009836 A1* | 1/2008 | Fiering | A61M 5/14276 604/891.1 |
| 2008/0065002 A1 | 3/2008 | LObl et al. | |
| 2009/0259267 A1 | 10/2009 | Jolly | |
| 2009/0324552 A1* | 12/2009 | Lichter | A61K 31/00 424/93.4 |
| 2011/0245714 A1 | 10/2011 | Volckaerts | |
| 2011/0295194 A1 | 12/2011 | Fiering et al. | |
| 2015/0005843 A1 | 1/2015 | Polak | |
| 2015/0126900 A1 | 5/2015 | Walraevens et al. | |
| 2015/0157837 A1 | 6/2015 | Fiering et al. | |
| 2015/0289787 A1 | 10/2015 | Buchman et al. | |
| 2016/0136400 A1 | 5/2016 | Gibson | |
| 2016/0238617 A1* | 8/2016 | Parham | G01N 33/6893 |
| 2017/0246481 A1* | 8/2017 | Mishelevich | A61N 2/008 |

OTHER PUBLICATIONS

International Search Report & Written Opinion for PCT/IB2019/052225, mailed Aug. 2, 2019.

Alec Salt et al., "Perilymph pharmacokinetics of marker applied through a cochlear implant in guinea pigs," PLoS One, Aug. 17, 2017.

Office Action for China Application No. 201980020568.0, mailed Sep. 25, 2023.

Office Action for China Application No. 201980020568.0, mailed Apr. 22, 2024.

Dalian Ding et al., "Ethacrynic acid is the key for opening of the blood-labyrinth barrier," Chinese Journal of Otology, Jan. 2004, vol. 2, No. 1.

* cited by examiner

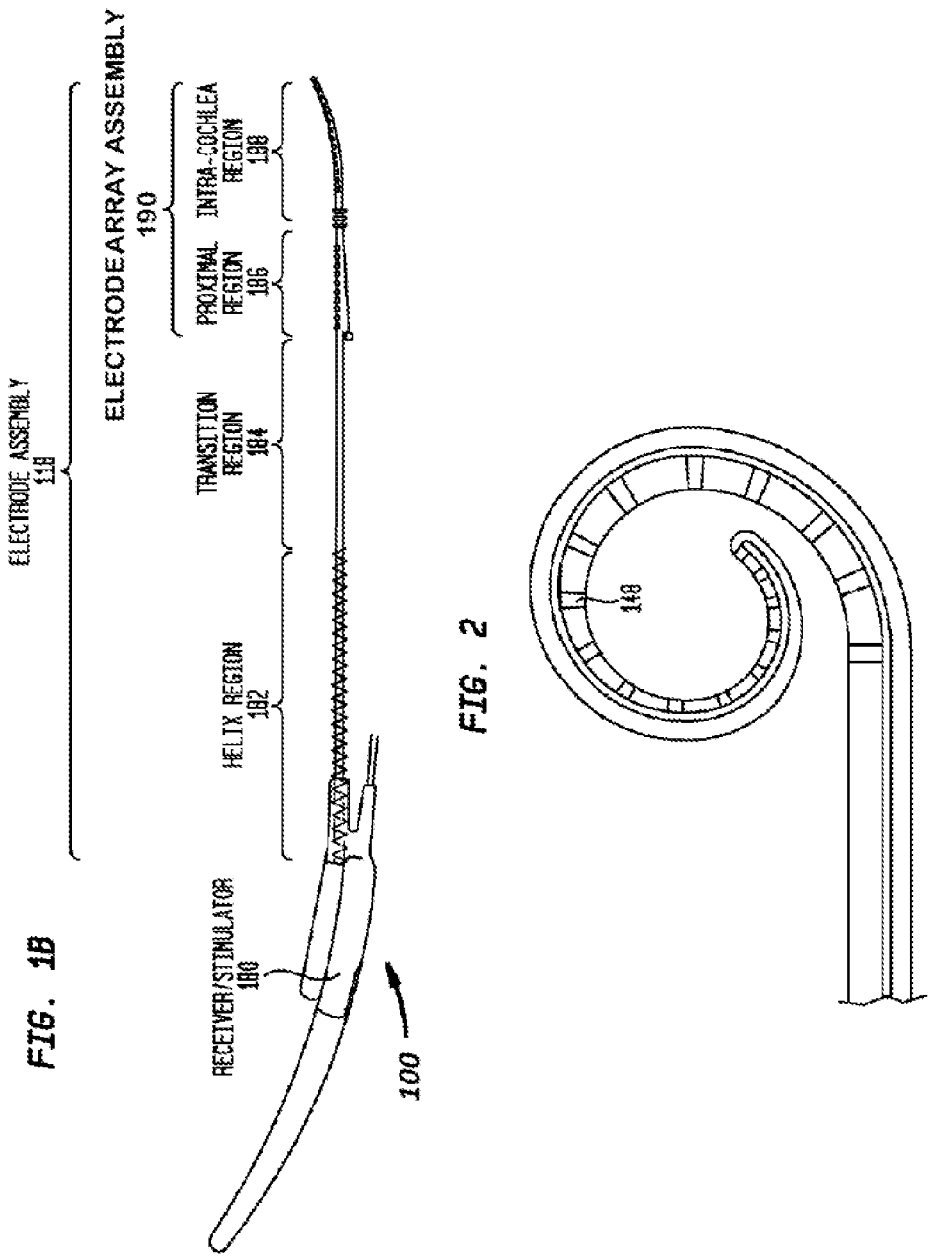

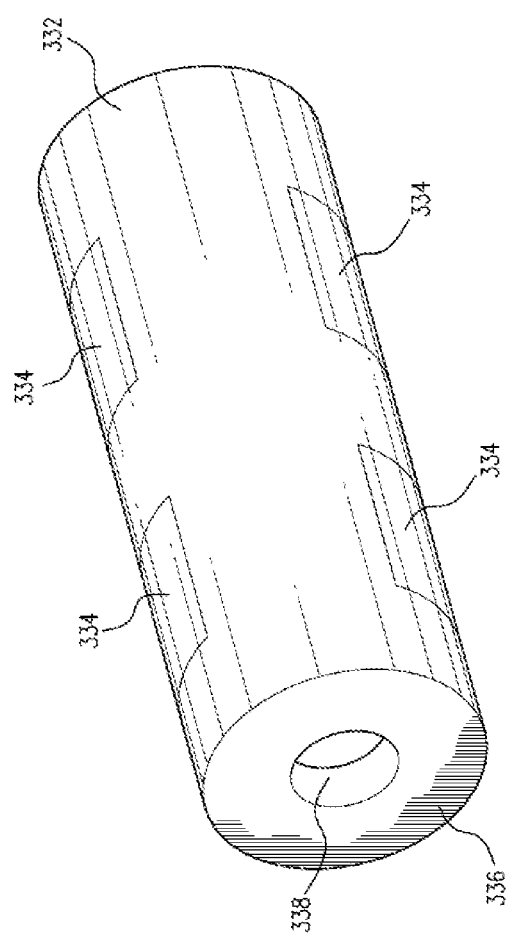

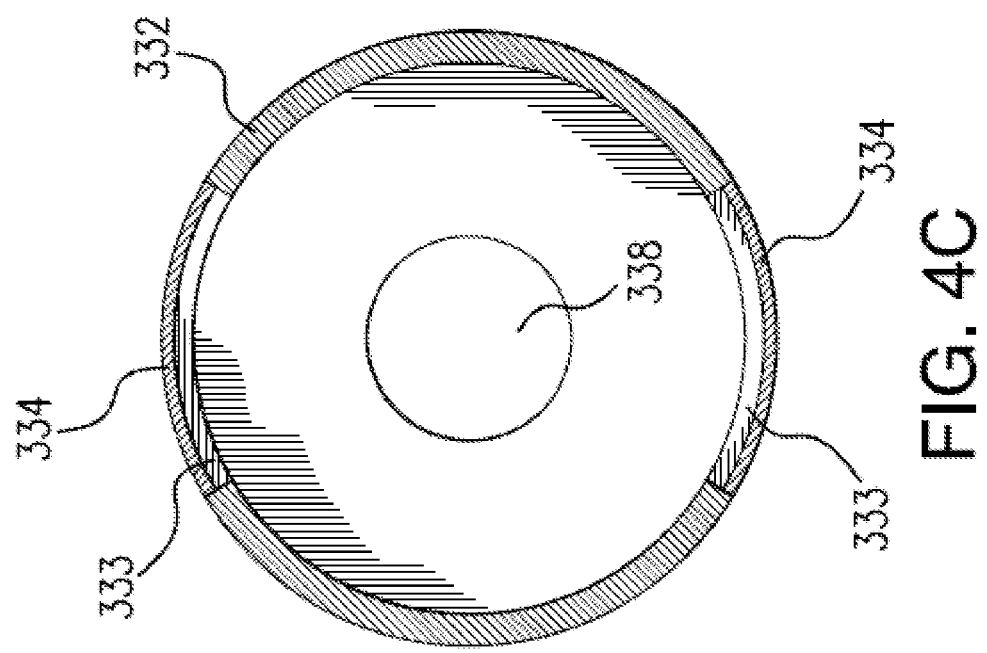

PROSTHESIS MANAGEMENT OF BODY PHYSIOLOGY

CROSS-REFERENCE TO RELATED APPLICATIONS

This application claims priority to U.S. Provisional Application No. 62/645,455, entitled PROSTHESIS MANAGEMENT OF BODY PHYSIOLOGY, filed on Mar. 20, 2018, naming Daniel SMYTH of Mechelen, Belgium as an inventor, the entire contents of that application being incorporated herein by reference in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

Many devices, such as medical devices that interface with a recipient, have structural and/or functional features where there is utilitarian value in adjusting such features for an individual recipient. The process by which a device that interfaces with or otherwise is used by the recipient is tailored or customized or otherwise adjusted for the specific needs or specific wants or specific characteristics of the recipient is commonly referred to as fitting. One type of medical device where there is utilitarian value in fitting such to an individual recipient is the above-noted cochlear implant. That said, other types of medical devices, such as other types of hearing prostheses, exist where there is utilitarian value in fitting such to the recipient.

SUMMARY

In accordance with an exemplary embodiment, there is an implantable device configured to cause trauma to an inner ear and/or a middle ear recipient. In some embodiments, the trauma is reversible, and in others, it is not reversible.

In accordance with another exemplary embodiment, there is a method, comprising monitoring a physical phenomenon inside a cochlea of a recipient; and managing a blood labyrinth barrier of the recipient based on the monitored physical phenomenon.

In accordance with another exemplary embodiment, there is a method, comprising administering a therapeutic substance to a person, and inflicting trauma and/or inducing a foreign body response in or proximate an anatomical structure of the person, thereby adjusting a concentration and/or amount of the therapeutic substance in the anatomical structure relative to that which would be the case in the absence of the trauma and/or foreign body response.

In accordance with another exemplary embodiment, there is a system, comprising an implantable blood labyrinth barrier management component configured to influence the blood labyrinth barrier to control an amount of a substance in an anatomical structure beyond that which would be the case in the absence of the influence.

BRIEF DESCRIPTION OF THE DRAWINGS

Embodiments are described below with reference to the attached drawings, in which:

FIG. 2 depicts a side view of a cochlear implant electrode array in a curled configuration;

FIGS. 4A-4C depict some exemplary features of a portion of the cochlear implant electrode array of FIG. 3A;

DETAILED DESCRIPTION

Figure 1:
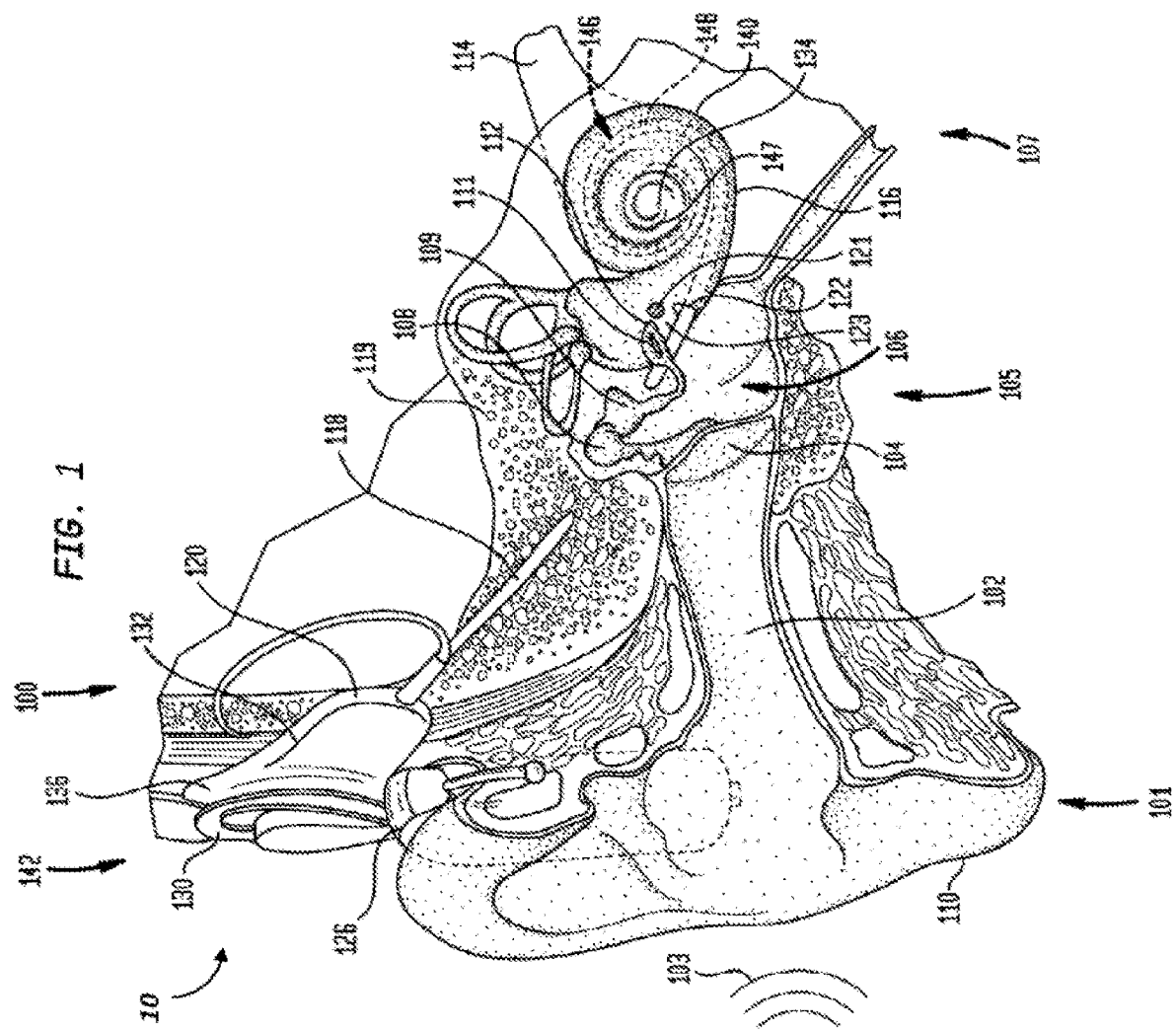
FIG. 1A is a perspective view of an exemplary hearing prosthesis in which at least some of the teachings detailed herein are applicable.
FIG. 1B depicts a side view of the cochlear implant 100 outside of the recipient.
Figure 1A:
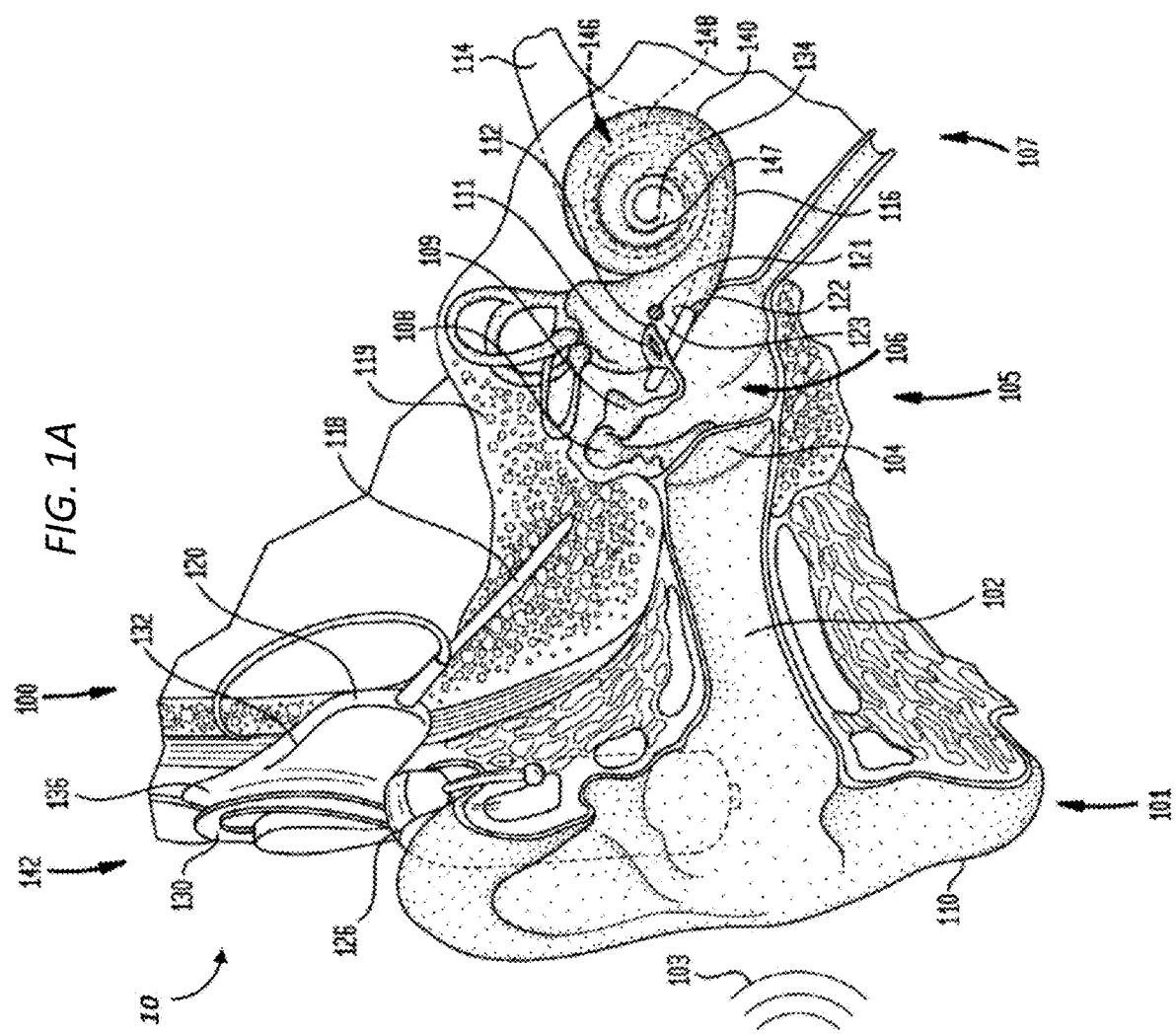

FIG. 1A is a perspective view of a cochlear implant, referred to as cochlear implant 100, implanted in a recipient, to which some embodiments detailed herein and/or variations thereof are applicable. The cochlear implant 100 is part of a system 10 that can include external components in some embodiments, as will be detailed below. Additionally, it is noted that the teachings detailed herein are also applicable to other types of hearing prostheses, such as by way of example only and not by way of limitation, bone conduction devices (percutaneous, active transcutaneous and/or passive transcutaneous), direct acoustic cochlear stimulators, middle ear implants, and conventional hearing aids, etc. Indeed, it is noted that the teachings detailed herein are also applicable to so-called multi-mode devices. In an exemplary embodiment, these multi-mode devices apply both electrical stimulation and acoustic stimulation to the recipient. In an exemplary embodiment, these multi-mode devices evoke a hearing percept via electrical hearing and bone conduction hearing. Accordingly, any disclosure herein with regard to one of these types of hearing prostheses corresponds to a disclosure of another of these types of hearing prostheses or any medical device for that matter, unless otherwise specified, or unless the disclosure thereof is incompatible with a given device based on the current state of technology. Thus, the teachings detailed herein are applicable, in at least some embodiments, to partially implantable and/or totally implantable medical devices that provide a wide range of therapeutic benefits to recipients, patients, or other users, including hearing implants having an implanted microphone, auditory brain stimulators, pacemakers, visual prostheses (e.g., bionic eyes), sensors, drug delivery systems, defibrillators, functional electrical stimulation devices, etc.

In view of the above, it is to be understood that at least some embodiments detailed herein and/or variations thereof are directed towards a body-worn sensory supplement medical device (e.g., the hearing prosthesis of FIG. 1A, which supplements the hearing sense, even in instances when there are no natural hearing capabilities, for example, due to degeneration of previous natural hearing capability or to the lack of any natural hearing capability, for example, from birth). It is noted that at least some exemplary embodiments of some sensory supplement medical devices are directed towards devices such as conventional hearing aids, which supplement the hearing sense in instances where some natural hearing capabilities have been retained, and visual prostheses (both those that are applicable to recipients having some natural vision capabilities and to recipients having no natural vision capabilities). Accordingly, the teachings detailed herein are applicable to any type of sensory supplement medical device to which the teachings detailed herein are enabled for use therein in a utilitarian manner. In this regard, the phrase sensory supplement medical device refers to any device that functions to provide sensation to a recipient irrespective of whether the applicable natural sense is only partially impaired or completely impaired, or indeed never existed.

The recipient has an outer ear 101, a middle ear 105, and an inner ear 107. Components of outer ear 101, middle ear 105, and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear channel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109, and the stapes 111. Bones 108, 109, and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1A with an external device 142, that is part of system 10 (along with cochlear implant 100), which, as described below, is configured to provide power to the cochlear implant, where the implanted cochlear implant includes a battery that is rechargeable via the transcutaneous link.

In the illustrative arrangement of FIG. 1A, external device 142 can comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1A, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 1A is merely illustrative, and other external devices may be used with embodiments of the present invention.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand or multi-strand platinum or gold wire.

Cochlear implant 100 further comprises a main implantable component 120 and an elongate electrode assembly 118. In some embodiments, internal energy transfer assembly 132 and main implantable component 120 are hermetically sealed within a biocompatible housing. In some embodiments, main implantable component 120 includes an implantable microphone assembly (not shown) and a sound processing unit (not shown) to convert the sound signals received by the implantable microphone in internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120). In at least some embodiments, the teachings detailed herein and/or variations thereof can be utilized with any type of implantable microphone arrangement.

Main implantable component 120 further includes a stimulator unit (also not shown) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments, electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

FIG. 1B is a side view of a cochlear implant 100 without the other components of system 10 (e.g., the external components). Cochlear implant 100 comprises a receiver/stimulator 180 and an electrode assembly or lead 118. Electrode assembly 118 includes a helix region 182, a transition region 184, a proximal region 186, and an intra-cochlear region 188. Proximal region 186 and intra-cochlear region 188 form an electrode array assembly 190. In an exemplary embodiment, proximal region 186 is located in the middle-ear cavity of the recipient after implantation of the intra-cochlear region 188 into the cochlea. Thus, proximal region 186 corresponds to a middle-ear cavity sub-section of the electrode array assembly 190. Electrode array assembly 190, and in particular, intra-cochlear region 188 of electrode array assembly 190, supports a plurality of electrode contacts 148. These electrode contacts 148 are each connected to a respective conductive pathway, such as wires, PCB traces, etc. (not shown) which are connected through lead 118 to receiver/stimulator 180, through which respective stimulating electrical signals for each electrode contact 148 travel.

Figure 3A:
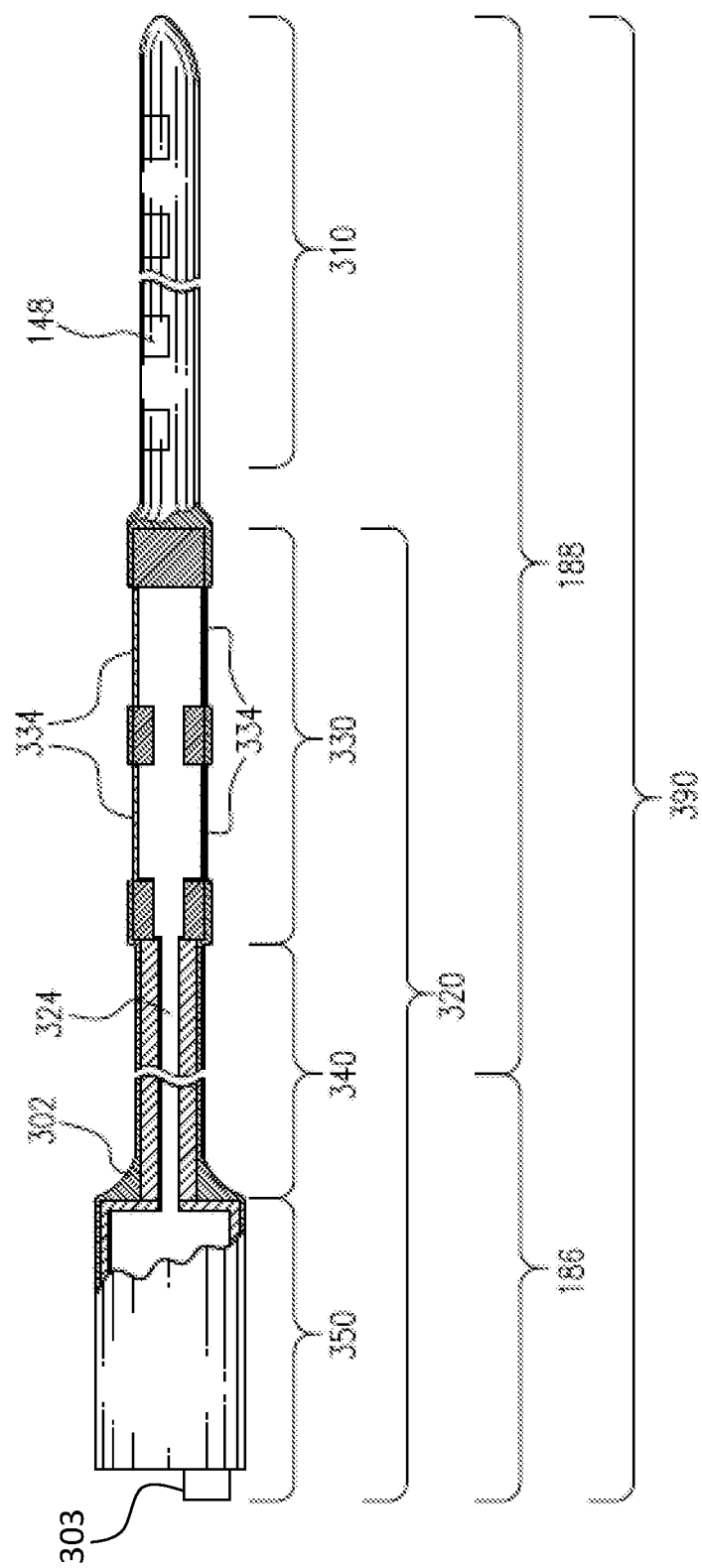
FIG. 3A depicts an exemplary cochlear implant electrode array according to an exemplary embodiment.

FIG. 2 is a side view of electrode array assembly 190 in a curled orientation, as it would be when in situ in a patient's cochlea, with electrode contacts 148 located on the inside of the curve. FIG. 3A depicts a side view of a device 390 corresponding to a cochlear implant electrode array assembly that can include some or all of the features of electrode array assembly 190 of FIG. 1B. More specifically, in an exemplary embodiment, electrode assembly 118 includes electrode array assembly 390 instead of electrode array assembly 190 (i.e., 190 is replaced with 390). Thus, according to an exemplary embodiment, there is a cochlear implant 100 as detailed above, which includes electrode array assembly 390, where the electrodes of the electrode array assembly 390 are in communication with the remaining portions of the implantable component of the cochlear implant in a conventional manner (albeit the leads or the like are potentially rerouted about the electrode array assembly 390 in order to accommodate the teachings detailed herein and/or variations thereof). Additional details of assembly 390 will now be provided.

Electrode array assembly 390 includes a cochlear implant electrode array 310 and an apparatus 320 configured to cause trauma in a cochlea. In an exemplary embodiment, the apparatus induces a foreign body response in the cochlea. In an exemplary embodiment, the trauma induces the foreign body response in the cochlea, while in other exemplary embodiments, the trauma does not induce the foreign body response. In an exemplary embodiment, it does one and not the other, and in other embodiments, it does both. In an exemplary embodiment, the trauma is reversible. In an exemplary embodiment, the trauma is not reversible or at least not completely reversible. In an exemplary embodiment, the trauma is at least 30%, 40%, 50%, 60%, 70%, 80%, 90%, 91%, 92%, 93%, 94%, 95%, 96%, 97%, 98%, 99% or more reversible. In an exemplary embodiment, the trauma is 100% reversible. In an exemplary embodiment, the foreign body response is beyond that which would result from the mere insertion/implantation process of inserting the cochlear electrode array. In an exemplary embodiment, the foreign body response is a foreign body response that is purposely exaggerated beyond that which would result from the insertion/implantation of the electrode array. That is, the foreign body response is purposely induced to be more severe than otherwise would be the case. In an exemplary embodiment, the foreign body response is a process that results from something that is at least partially reversible, such as at least 30%, 40%, 50%, 60%, 70%, 80%, 90%, 91%, 92%, 93%, 94%, 95%, 96%, 97%, 98%, 99% or more reversible. In an exemplary embodiment, the foreign body response is a foreign body response that results from something that is atraumatic. In an exemplary embodiment, the foreign body response is a foreign body response that results from something that is not traumatic. In an exemplary embodiment, electrode array assembly 390 has some and/or all of the functionality of electrode array assembly 190, where electrode array assembly 190 corresponds to a state-of-the-art electrode array assembly and/or variations thereof and/or an earlier model electrode array assembly. By way of example only and not by way of limitation, electrode array assembly 390 includes any electrode array 310 comprising a plurality of electrodes 148. The electrode array assembly 390 is configured such that the electrodes 148 of the electrode array 310 are in and/or can be placed in signal communication with the receiver stimulator 180. Hereinafter, any disclosure of trauma corresponds to, in an alternative embodiment, inducing a foreign body response, and vice versa, unless otherwise noted in providing that the art enables such. To be clear, this is not to say that the two are the same. Just the opposite. The purpose of this statement is simply to provide a shorthand way of conveying the various concepts. It is also noted that the two are not mutually exclusive. Trauma can cause a foreign body response.

In some embodiments, the apparatus 320 is configured to expand to contact a wall of the cochlea. In an exemplary embodiment of FIG. 3A, the apparatus 320 is a pressure based assembly. Along these lines, in an exemplary embodiment, the apparatus 320 is configured to expand upon pressurization of components thereof.

Figure 3B:
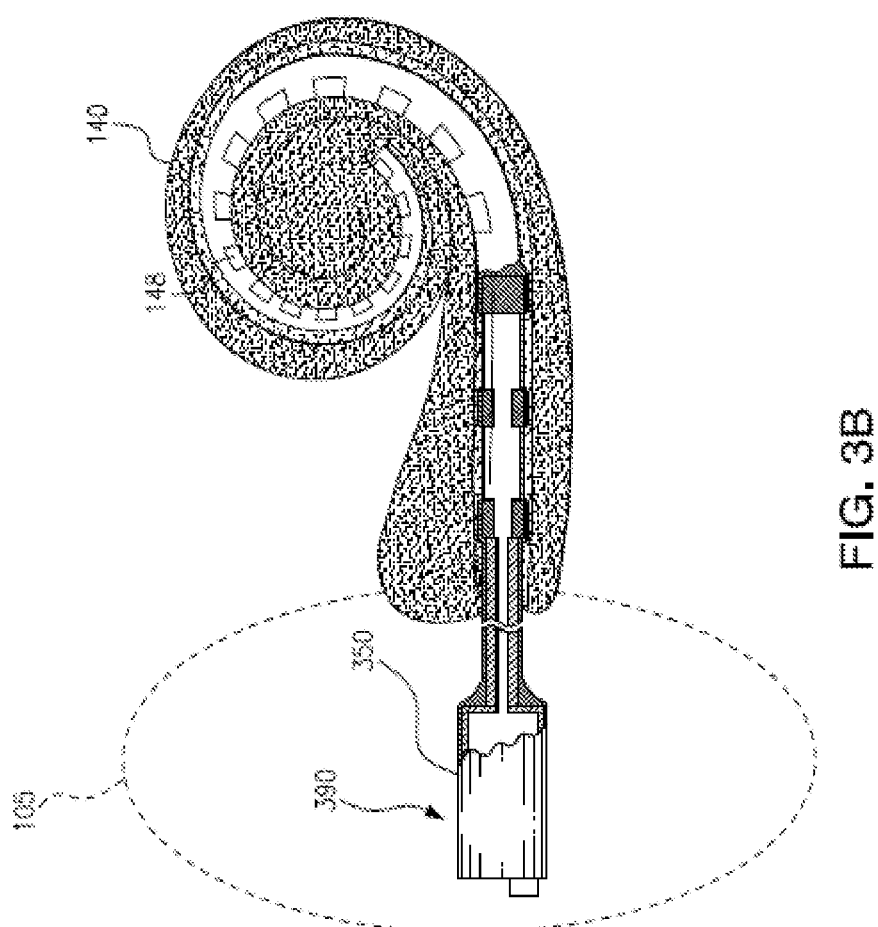
FIG. 3B depict the exemplary cochlear implant electrode array inserted into the cochlea.

More particularly, apparatus 320 includes an inflatable sub-assembly 330 which is in fluid communication with conduit 340 which is in turn is in fluid communication with pressure generator sub-assembly 350 (e.g., a pump coupled to a reservoir of a fluid). As can be seen, the pressure generator subassembly 350 includes electrical lead port 303 that places the pressure generator subassembly into electrical communication with the receiver stimulator of the cochlear implant. That said, in an exemplary embodiment, component 350 can be FIG. 3B depicts a conceptual representation of the electrode array assembly 390 inserted into a cochlea 140 that is configured to prosthetically remain in the cochlea (that is it is configured to remain in the cochlea for a time period concomitant with the use of a prosthetic device, as opposed to a temporary insertion such as might be the case for a needle or the like). FIG. 3B depicts a conceptual drawing depicting the intra-cochlea region 188 of the electrode array assembly 390 in the cochlea 140, and the proximal region 186 of the electrode array assembly 390 located outside the cochlea 140, where the conduit 340 of the apparatus 320 extends from inside the cochlea 140 to outside the cochlea into the middle ear cavity, which is functionally represented by the dashed enclosure 105. It is noted that this drawing in FIGS. 3B and 3A is just that—conceptual, and are provided at least for the purpose of presenting the concept of the cochlear implant electrode array having apparatus 320 that is only partially inserted into the cochlea. In an exemplary embodiment, the electrode array assembly along with the inflatable sub-assembly (hereinafter, inflator) is inserted into the scala tympani. That said, in an alternate embodiment, at least the inflator is inserted into the scala vestibuli. Accordingly, in an exemplary embodiment, there is an electrode array assembly configured such that the electrode array is insertable into the scala tympani, and the inflator is insertable into the scala vestibule. In an exemplary embodiment, the entire electrode array assembly is configured to be insertable into the scala vestibuli.

Additional details of components of the assembly 390 will now be described.

Before describing some of the details of the array 390, it is briefly noted that this is presented in terms of a conceptual device. For example, it can be seen that the inflator 330 is located at the basil portion of the electrode array. More accurately, it can be seen that the inflator 330 is located only at the basil portion of the electrode array. In some embodiments, the inflator 330 is located midway along the electrode array, such as after the first 11 electrodes (thus, in an exemplary embodiment, in between two groups of 11 electrodes of a 22 electrode array). In some embodiments, the inflator can be located at the apical end of the electrode array. The inflator can be located anywhere there can be utilitarian value in placing such. Note also that while the embodiment depicts the inflator as a discreet component located only at one location, in an exemplary embodiment, multiple inflators as can be utilized and located along the electrode array. It is also noted that while the embodiment described herein details a pressure generator 350 that is located proximate the electrode array/part of the electrode array, in an exemplary embodiment, the pressure generator is located remotely from the electrode array, such as, by way of example only and not by way of limitation, in the receiver stimulator. Indeed, in this exemplary embodiment, a tube or conduit can extend along the electrode leads from the electrode array to the receiver stimulator, where a pump can be located.

In an exemplary embodiment, the pump is an electric pump that is operated as a result of the inductance field that is communicated transcutaneously to the receiver stimulator unit. In an exemplary embodiment, the pump can be a manual operated pump. Indeed, in an exemplary embodiment of the embodiment where the pump is located remotely from the electrode array assembly, the receiver stimulator can be configured with a flexible component that can be depressed repeatedly through the skin of the recipient. For example, the recipient can press his or her finger against his or her skin over top of the flexible component so as to pump fluid to the inflator.

In the exemplary embodiment, the inflator 330 is made up of a titanium cylinder 332 having a closed end and an end 336 that is open via port 338. Port 338 provides fluid communication between the inside of the cylinder and the outside of the cylinder. Inflator 330 includes four membranes 334 arrayed about the longitudinal surface of the cylinder. (The membranes are depicted as curved membranes, but, in alternate embodiments, the membranes are flat, or can be other shapes.) In the embodiments of the figures, the membranes 334 cover through holes 333 that extend through the longitudinal surface of the cylinder 332. The membranes 334 hermetically seal these holes. The membranes 334 are configured to deflect or otherwise move as a result of pressure variations inside the titanium cylinder due to the pump in the pressure generator sub-assembly 350. This causes pressure fluctuations within the inflator 330. In an exemplary embodiment, this is because the increased pressure in the cylinder 332 causes deflections of one or more membranes 334 outward.

In the embodiment of the figures, there are four separate membranes provided with the inflator 330. These membranes are evenly spaced laterally about the longitudinal axes of the cylinder 332, as can be seen. Some embodiments can use fewer or more membranes. In an exemplary embodiment, one, two, three, four, five, six or more membranes can be utilized. Any number of membranes that can enable the teachings detailed herein and/or variations thereof can be utilized in at least some embodiments.

Figure 4B:
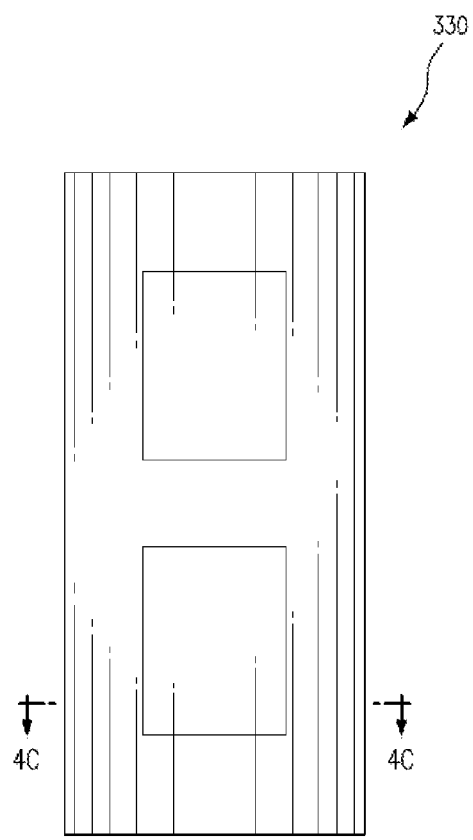

In the embodiments of FIGS. 4A to 4C, the membranes 334 are depicted as individual membranes. In some exemplary embodiments, these membranes can be welded or glued or crimped, etc., to the cylinder 332. In an exemplary embodiment, a membrane assembly is utilized, where the membrane is held within a frame, which frame is attached to the cylinder 332. Any device, system, or method that will enable the membranes to be attached to the cylinder 332 such that the teachings detailed herein can be practice can be utilized in at least some embodiments. Indeed, along these lines, in an exemplary embodiment, the cylinder 332 comprises four through holes. A single membrane sheet is wrapped around the cylinder 332. An adherence process can be utilized to adhere the membrane to the cylinder 332. The process adheres the sheet to the portions of the cylinder where there are no holes present. Thus the sheet is free to flex over the holes of the cylinder 332 as a result of pressure changes. Thus, four membranes are obtained from a manufacturing process were only one sheet is utilized.

Figure 5:
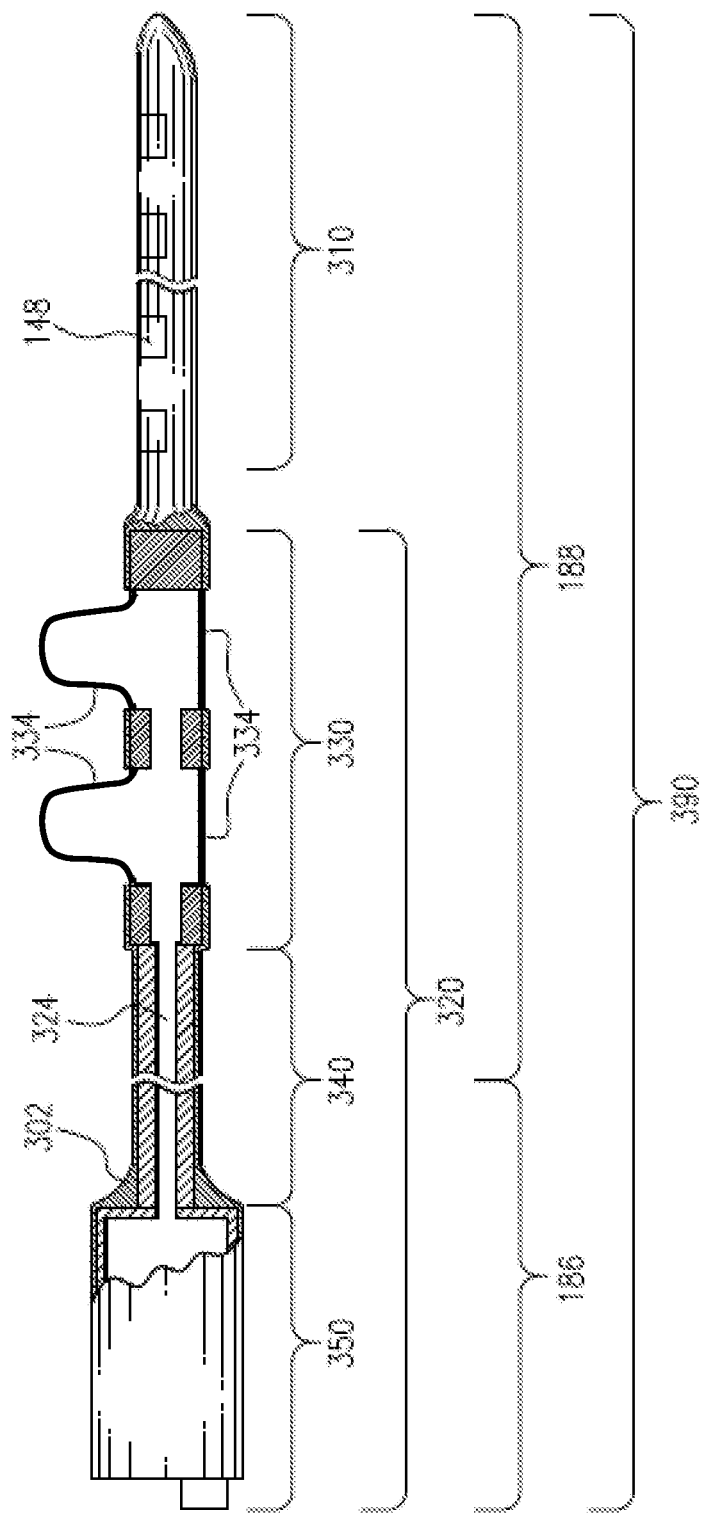
FIG. 5 depicts an exemplary embodiment of the cochlear implant electrode array of FIG. 3A in use.

FIG. 5 depicts an exemplary scenario of the utilization of the array 390 where two of the membranes 334 are extended outward/inflated. In practice, in at least some embodiments, all four of the membranes would be inflated. In some respects, this figure is presented to convey the general concept of inflation. That said, in some embodiments, it is noted that fewer than all of the membranes will in fact be inflated—such can be achieved via the utilization of certain types of material that are different for some membranes than others (and thus, more accurately, the inflation amounts can be different). A more rigid material can be utilized for one membrane as opposed to the other, and thus the amount of deformation will be different for the given pressure. In an exemplary embodiment, the pressure generator 350 pumps an inert gas through duct 324 to increase the pressure inside the cylinder 332, thus expanding the membranes 334 outward. In an exemplary embodiment, the membranes 334 expand to contact the walls of the cochlea. In some embodiments, the mere fact that the membranes are in contact with the wall of the cochlea is sufficient to cause the trauma and/or evoke/induce the foreign body response. In an exemplary embodiment, the membranes are expanded and contracted repeatedly so as to "tap" the walls of the cochlea, which tapping will eventually result in the induction of the trauma and/or the evocation of the foreign body response. In an exemplary embodiment, the membranes can be undulated so as to rub against the wall of the cochlea back and forth. In this regard, in an exemplary embodiment, the membranes can be configured such that upon reaching a certain pressure, one side of the membrane will expand more than the other, and thus this expansion will rub against the wall of the membrane in at least one direction because the other portion that is no longer expanding will be stationary relative to the wall.

In an exemplary embodiment, the membranes can have barbs or spikes or bumps or an abrasive surface thereon which, when expanded to the walls of the cochlea, will cause irritation of the like so as to result in the trauma or the foreign body response.

It is noted that the embodiments of FIGS. 3A-5 are but exemplary. In some alternate embodiments, the electrode array can be configured with other types of devices that will cause the trauma and/or evoke/induce the foreign body response. By way of example only and not by way of limitation, an optical/light producing device can be utilized to cause the trauma and/or evoke/induce the foreign body response. In this regard, fiber optics or the like can be utilized to route light into the inside of the cochlea that will cause/induce the trauma/response. In an alternate embodiment, the electrode array can be a common cochlear implant electrode array where the electrodes are utilized to cause/induce the trauma/response. In an exemplary embodiment, the cochlear implant can be configured such that the electrode array can be utilized to generate current at higher amperage levels than that which would be utilized to evoke a hearing percept in a normally functioning cochlear implant and/or can be applied at higher and/or lower alternating current frequencies than that which would be utilized to evoke a hearing percept in a normally functioning cochlear implant. In an exemplary embodiment, the cochlear implant can be configured such that the electrode array can be utilized to generate a direct current, at least for a limited period of time. Direct current is not a good type of current to apply to tissue inside a human being. In this regard, the direct-current can be utilized to cause/induce the trauma/response.

Any device, system, and/or method that can result in inducing trauma and/or evoking a foreign body response or any other type of physical phenomenon inside the human being to practice one or more of the teachings detailed herein can be utilized in at least some exemplary embodiments. Also, any device that can manage the blood labyrinth barrier can be utilized in some embodiments, even if such does not result in trauma and/or a foreign body response. Any device that can cause inflammation or otherwise that will alter the blood labyrinth barrier (e.g., by inflaming the blood labyrinth barrier) can be used in some embodiments.

Figure 6:
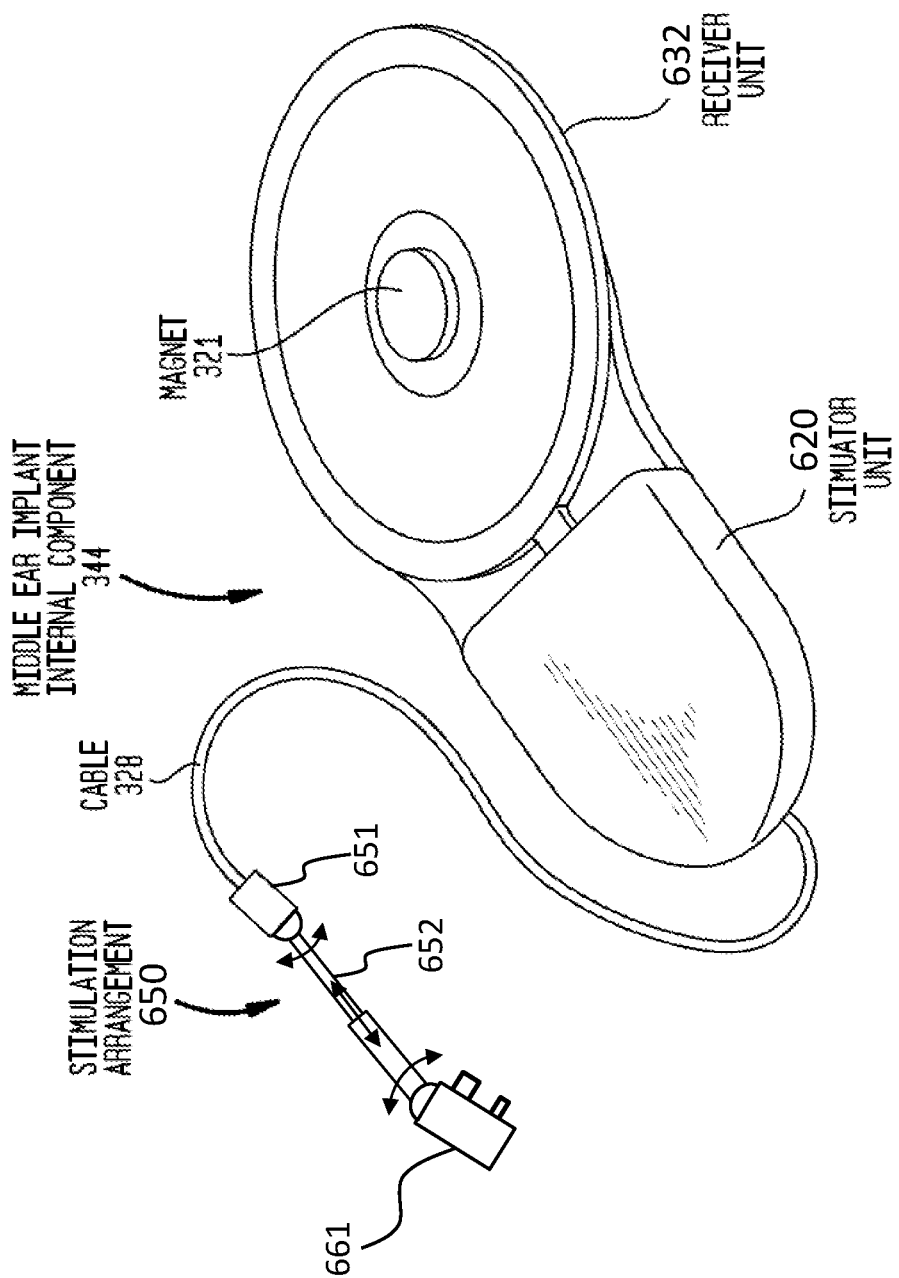
FIGS. 6 and 7 present alternate exemplary embodiments of an implantable component configured to execute at least some of the method actions detailed herein.

FIG. 6 is a perspective view of an exemplary internal component 344 of an implant that has the trauma causing/foreign body response inducing/evoking components in the middle ear when implanted. Internal component 344 comprises an internal receiver unit 632, a modified stimulator unit 620 and a stimulation arrangement 650. In an exemplary embodiment, the modified stimulator unit can be a stimulator unit of a middle ear implant that has been modified, such as by reprogramming, to actuate the stimulation arrangement 650 as opposed to actuating a middle ear actuator or the like. In some alternative embodiments, the stimulator unit can be a processor with output to cable 328, where the processor receives input via the receiver unit 632 processes that input according to an algorithm therein (e.g., if a frequency is received at a certain amplitude, the processor well put a signal controlling stimulation arrangement 650 in a manner. As shown, receiver unit 632 comprises an internal coil (not shown), and a magnet 320 fixed relative to the internal coil. In some embodiments, internal receiver unit 632 and modified stimulator unit 620 are hermetically sealed within a biocompatible housing. This housing has been omitted from FIG. 6 for ease of illustration.

Stimulator unit 620 is connected to stimulation arrangement 650 via a cable 328. Stimulation arrangement 650 comprises an actuator assembly 661, an actuator assembly mount member 651, and an actuator assembly positioning arm 652. In an exemplary embodiment, actuator assembly mount member 651 is configured to be located in an artificial passageway in mastoid bone and fixed to the mastoid bone of the recipient. As indicated by the curved arrows of FIG. 6, the actuator assembly mount member 651 and the actuator assembly 661 are configured to enable articulation of the actuator assembly positioning arm 652 relative to those components. Further, as indicated by the straight arrow of FIG. 6, the actuation assembly positioning arm 652 is configured to telescope to provide longitudinal adjustment between the actuator assembly 661 and the actuator assembly mount member 651.

In operation, actuator 661 applies stimulation to the round window and/or oval window and/or another component of the outer wall of the cochlea in a manner that results in the trauma and/or in a manner that results in evoking/inducing a foreign body response. In some embodiments, the body of the actuator assembly 661 remains fixed relative to the outer wall of the cochlea, and one or both of the output arms (two are shown, one for the round window and one for the oval window, but in some embodiments, there is only one output for the round window or the oval window) applies stimulation to the respective round and oval windows. That said, in an alternative embodiment, the actuator assembly mount member along with the other components can swing or otherwise cause the actuator 661 to strike the outer wall of the cochlea and/or the round and/or the oval window, much as someone would strike a board with a hammer or the like (or a manhole cover, with a hammer, etc.). In an exemplary embodiment, actuator 661 is replaced with some other form of component that results in the stimulation, such as, for example, a blunt object or a spiked object, etc. Any component or configuration that can induce trauma and/or induce the foreign body response can be utilized in at least some exemplary embodiments.

In an exemplary embodiment, the devices, systems, and/or methods detailed herein are configured so as to provide energy that generates waves of fluid motion of the perilymph, thereby inducing trauma/inducing the foreign body response in or at or associated with hair cells of the organ of Corti and/or causing trauma or inducing the foreign body response, at the organ of Corti. In an exemplary embodiment, this is achieved utilizing vibrations of sufficient magnitude or lack thereof at certain frequencies that can cause the aforementioned trauma and/or foreign body response. In an exemplary embodiment, this can correspond to a subsonic or a supersonic frequency that, provided over a sufficient period of time, can result in the trauma and/or the induction of the foreign body response. In some instances, the sound can be heard, but is presented briefly.

Figure 7:
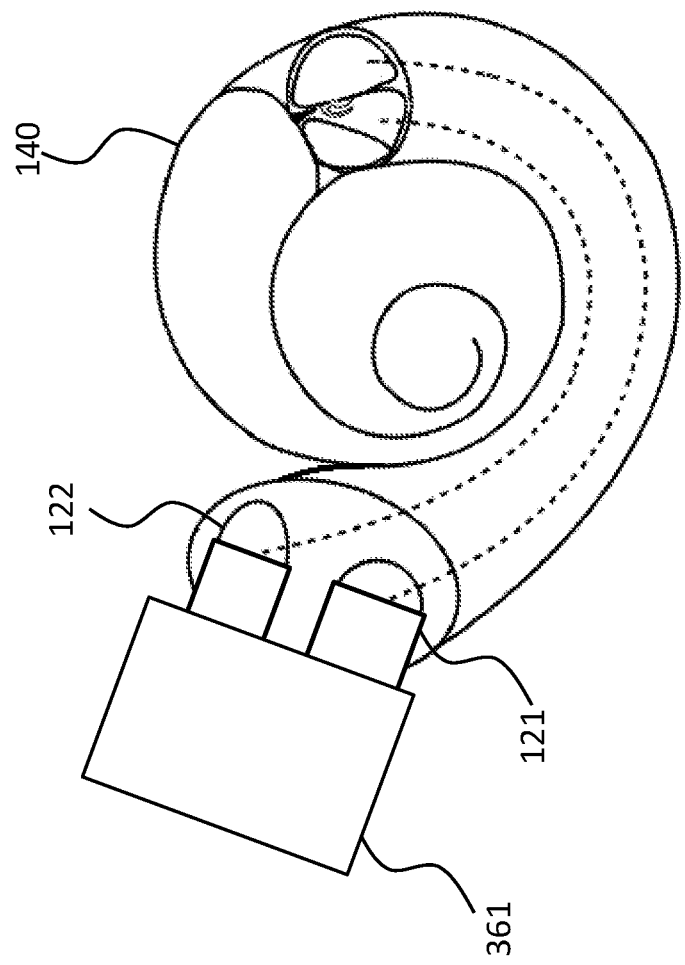

FIG. 7 depicts a high-level conceptual view of the utilization of the device of FIG. 6, where actuator 361 is position outside cochlea 140. In this exemplary embodiment, the actuator 361 is configured to apply a compression force and/or a tension force to the round window 121 and/or apply a compression force and/or a tension force to the oval window 122. This can be done in a synchronized matter can be done in a separate manner. In some embodiments, the forces correspond to a banging force as opposed to a more steady force (e.g., analogous to the utilization of a hammer or the like).

In view of the above, it can be seen that in an exemplary embodiment, there is an apparatus, comprising an implantable device configured to cause trauma to and/or induce a foreign body response in an inner ear and/or a middle ear of a recipient. With respect to the embodiment of FIG. 3A, it can be seen that in some exemplary embodiments, the implantable device is a cochlear implant. Conversely, as can be seen with respect to the embodiment of FIG. 6, in some embodiments, the implantable device is a component implanted in the middle ear.

In view of the above, along with the teachings below, it will be seen that in an exemplary embodiment, there is a device, system and/or method that enables the inflammation and/or the deflammation of the BLB for the control or otherwise management of the distribution of compounds or other substances in a body structure, such as the cochlea, the eye, the kidney, etc. In an exemplary embodiment, there are devices, systems, and/or methods that are configured to enable a modicum of control over the BLB such that the BLB can be opened and/or closed, thereby influencing a permeability of the barrier to the substances at issue. Such devices, systems, and/or methods can enable the systematic delivery of drugs or substances, enable the flushing of toxins from the structure at issue, such as for, for example, otoprotection. Such can also enable control or otherwise management over drug distribution and drug levels in the cochlea.

As noted above, in some embodiments, a mechanical stimulation/mechanical force output device can be utilized to evoke the trauma/foreign body response. Also as noted above, in some embodiments, an electrical stimulation/electrical output device can be utilized to evoke the trauma/foreign body response. Thus, in an exemplary embodiment, the implantable device is configured to extend into a cochlea of a recipient and electrically stimulate tissue inside the recipient to cause the trauma and/or induce the foreign body response. Still further, consistent with the embodiments detailed above, in some exemplary embodiments, the implantable device is a cochlear electrode array configured to extend into a cochlea of a recipient and to variously electrically stimulate tissue of the cochlear to evoke a hearing percept (concomitant with a typical operation of a cochlear implant) and to electrically stimulate tissue inside the recipient to cause the trauma and/or induce the foreign body response (which is not concomitant with a typical operation of a cochlear implant). It is noted that while some embodiments utilize electrodes located inside the cochlea to create the trauma and/or induce the foreign body response, in some embodiments, electrodes only located outside the cochlea are utilized. By way of example only and not by way of limitation, in an exemplary embodiment, one or more electrodes can be placed against the outer wall the cochlea in the middle ear, which can be utilized to induce the trauma and/or induce the foreign body response. In an exemplary embodiment, the electrode(s) can be the ECE/Hardball/return. In an exemplary embodiment, the electrode(s) could be placed against or otherwise proximate to the round window, the oval window, etc. Such can be placed against or otherwise proximate the round window niche. Still, in some embodiments, the electrodes can communicate with electrodes that are also inside the cochlea so as to close the circuit. Also, in some embodiments, the hardball or the return electrode/ECE can be utilized to close the circuit with the electrodes located in the middle ear and/or the electrodes located in the cochlea. Any arrangement that can be utilized to establish electrical stimulation cause trauma and/or induce a foreign body response in the inner ear and/or in the middle ear of a recipient can be utilized in at least some exemplary embodiments. FIG. 3A shows an exemplary embodiment an implantable device that is part of a cochlear implant configured to extend into a cochlea of a recipient and to variously electrically stimulate tissue of the cochlear to evoke a hearing percept and to electrically stimulate tissue inside the recipient to cause the trauma and/or induce the foreign body response without evoking a hearing percept. It is noted that in some embodiments, even a normal electrode array without the inflator 330 or other mechanical stimulation components can be utilized in at least some exemplary embodiments to cause the trauma and/or induce the foreign body response without evoking the hearing percept. The key here is that there can be utilitarian value with respect to causing the trauma/inducing the foreign body response without having the recipient "hear" something. That said, in some embodiments, the trauma/foreign body response can result in some hearing percept associated there with.

In some embodiments, the implantable device is configured to passively cause the trauma and/or induce the foreign body response. In some embodiments, the implantable device is configured to actively cause the trauma and/or induce the foreign body response.

Figure 8:
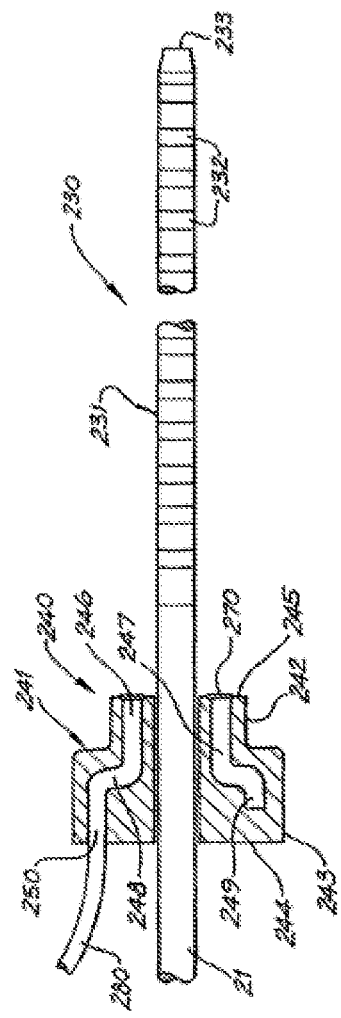
FIGS. 8 and 9 present alternate exemplary embodiments of an implantable component configured to execute at least some of the method actions detailed herein.

FIG. 8 depicts an exemplary alternate embodiment where the implantable device is a drug delivery device/substance deliver device combined with a cochlear implant electrode array, although in other embodiments, the implantable device is solely a drug delivery device. (In a similar vein, the mechanical stimulation apparatuses detailed above/subsystems detailed above can be utilized in an implantable device that is solely such (e.g., no electrode array to evoke a hearing percept. This is also the case with respect to the optical systems/light systems, etc. Any disclosure herein of any configuration can be utilized independently of or in combination with any other component disclosed herein.)

FIG. 8 depicts an assembly 230 includes an elongate member 231, corresponding to an electrode array (intracochlear portion) that has a distal end 233 that is firstly inserted into the cochlea upon insertion of the assembly 230. As depicted in FIG. 8, a collar 240 is located (e.g., slidably disposed or fixedly disposed) around the lead 21 (which can be the lead of FIG. 1A). The collar 240 is part of a system for delivering one or more substances (pharmaceutical or bioactive or other substances) to a location just external the cochlea (e.g., to the round or oval window, or to another location, such as to the cochleostomy, or any other utilitarian location). In some embodiments, the substance delivered is a substance that induces the foreign body response and/or causes the trauma. In some embodiments, the substance delivered is a therapeutic substance. More on this below.

The collar 240 has a stepped outer surface 241 defined by two cylindrical portions 242 and 243. In the depicted embodiment, the collar 240 is symmetrical about its longitudinal axis and has parallel proximal and distal ends 244, 245. An outlet 246 of the collar 240 is positioned in the distal end 245 of the collar 240. In the depicted embodiment, the collar 240 further has an inlet 250 in the proximal end 244 of the collar 240. The inlet and outlet are in communication, such as fluid communication, with each other. As depicted in FIG. 8, the outlet 246 of the collar 240 comprises an annular opening in the distal end 245 of the collar. The chamber 247 within the collar extends back into the collar 240 from the outlet 246. As the depicted outlet 246 is an annular opening, the chamber 247 is also annular in form and so comprises a cylindrical chamber having an outer and inner surface and extending back into the collar from the outlet 246. It will be appreciated, however, that the outlet and chamber need not be annular to fall within the scope of the present application.

The annular chamber 247 has a frusto-conical region 248 where the outer and inner walls of the chamber 247 move away from the longitudinal axis of the collar 240, and a further cylindrical region 249 distal the outlet. In this embodiment, the inlet 250 comprises a pipe extending from the proximal end 244 of the collar into the chamber 247. The inlet 250 is adjacent the outer wall 241 of the collar 240.

The distal end 233 of the elongate member can be firstly inserted into the cochleostomy of the implantee during placement of the implant. The chamber in the collar acts as a reservoir for a bioactive substance. This bioactive substance in the chamber diffuses from the chamber into the implantee through a semi-permeable membrane 270 in the outlet 246. The membrane 270 allows the bioactive substance to leach from the chamber during and/or following implantation to the desired site of action for the bioactive substance.

Where the bioactive substance is carried in or comprises a fluid, the semi-permeable membrane 270 allows the fluid to leach or diffuse therethrough.

The membrane 270 can act as a valve or metering device that allows fluid to exit the chamber but prevents, or at least substantially prevents, fluid flow from external the chamber back into the chamber within the body.

The embodiment of FIG. 8 presents an exemplary embodiment where the trauma causing/foreign body response inducing components are located outside the cochlea. While the embodiment of FIG. 8 presents a substance delivery device that causes the trauma/induces the foreign body response, in an alternate embodiment, the collar 240 can instead be a mechanical device or the like and/or an electrical stimulating device or the like. In an exemplary embodiment, the inflation system detailed above can be located at the left face of the collar so as to induce mechanical stimulation onto the outer wall the cochlea and/or on to the round and/or over windows of the cochlea, etc.

Figure 9:
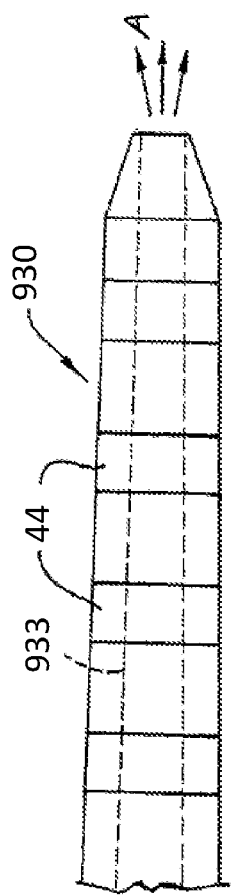

FIG. 9 presents another exemplary embodiment of an electrode array 930 that includes electrodes 44 that also includes a conduit 933 through which a substance is ejected, represented by the indicator/arrows "A." This exemplary embodiment presents a device that can enable the substance to be directed/supplied directly into the cochlea, as opposed to the embodiment of FIG. 8 where the substance is provided at the location outside the cochlea and can diffuse through the wall and/or through the windows to inside the cochlea. Corollary to this is that in an exemplary embodiment, the collar is configured with needles or the like that extend from outside the cochlea into the cochlea. Indeed, FIG. 9 can conceptually represent a needle that can be mounted at the outlet of the collar 240 (minus the electrodes, etc.) to inject or otherwise directly provide the substance into the cochlea.

It is also noted that in an exemplary embodiment, the electrode array can include a component that causes the electrode array to move within the cochlea. In an exemplary embodiment, a magnetorestrictive material can be utilized to cause the length of the electrode array to move like a whip or the like or to cause the electrode array to vibrate to cause the trauma and/or induce the foreign body response due to contact with the wall of the cochlea and/or due to the causation of fluid motion within the cochlea due to the perilymph that causes trauma to the walls of the cochlea.

It is noted that because the boundary between the inner ear and the middle ear may not necessarily be specifically defined (when does the wall of the cochlea ceased to be the middle ear and become the inner ear). Any disclosure herein with respect to inner ear trauma and/or foreign body response in the inner ear (cochlea) also corresponds to a disclosure of such at the boundary between the inner ear and the middle ear (e.g., the wall of the cochlea) unless otherwise stated. This is also the case with respect to any reference to middle ear trauma and/or foreign body response in the middle ear.

As will be described in greater detail below, there can be utilitarian value with respect to determining whether or not a condition exists within the recipient that would warrant the action of causing trauma and/or inducing the foreign body response relative to another condition where the absence of that condition which would not warrant the action. Thus, in an exemplary embodiment, there is an implantable device that is configured to detect a physical phenomenon inside a cochlea. In this exemplary embodiment, the implantable device is configured to cause the trauma and/or induce the foreign body response upon the detection of the physical phenomenon. Corollary to this is that in an exemplary embodiment, the implantable device is configured to not cause the trauma and/or induce the foreign body response upon the lack of detection of that physical phenomenon. In this regard, in an exemplary embodiment, instead of element 330 being an inflator, element 330 can be a detector or a receptor. In an exemplary embodiment, element 330 can include diaphragms the like that can react to a change in pressure inside the cochlea. Because the diaphragms 330 are in fluid communication with element 350, in an exemplary embodiment, element 350 can be a pressure detector or the like that can evaluate the pressure inside the cochlea because the pressure inside the detector or receptor will change with pressure change inside the cochlea owing to the resilient nature/flexibility of the diaphragms 334. Indeed, in an exemplary embodiment, the embodiment where elements 334 are membranes can be utilized, and the pump 350 can be a combination pump/pressure detector. In an exemplary embodiment, upon a determination that the pressure inside the inner ear has changed or otherwise is at a value for a specific period of time that would be indicative of a is a phenomenon (e.g., an ailment, an infection, etc.), because the pressure detector 350 is in signal communication with the processor of the receiver simulator via lead output 303, the processor which is programmed to evaluate the output signal can determine that the pressure has changed for a sufficient period of time such that the trauma should be caused and/or the foreign body response should be induced.

In an exemplary embodiment, element 330 can be a temperature sensor, or, in an exemplary embodiment, a temperature sensor can be a component that is delta to the components of FIG. 3A. In an exemplary embodiment, the temperature sensor can detect the temperature inside the cochlea. Monitoring such can determine whether or not there is a increased temperature within the cochlea, which can be indicative of an infection or the like inside the cochlea.

The exemplary embodiment of FIG. 3A where element 330 is a pressure detector and is not a trauma causing/foreign body response inducing device, in some embodiments, the electrodes 148 can be utilized to cause the trauma, etc. That said, in an exemplary embodiment, the trauma is not caused by the implantable device but instead is caused by another type of device. In this regard, in an exemplary embodiment, the implantable device is a device that only the text the physical phenomenon.

Figure 10:
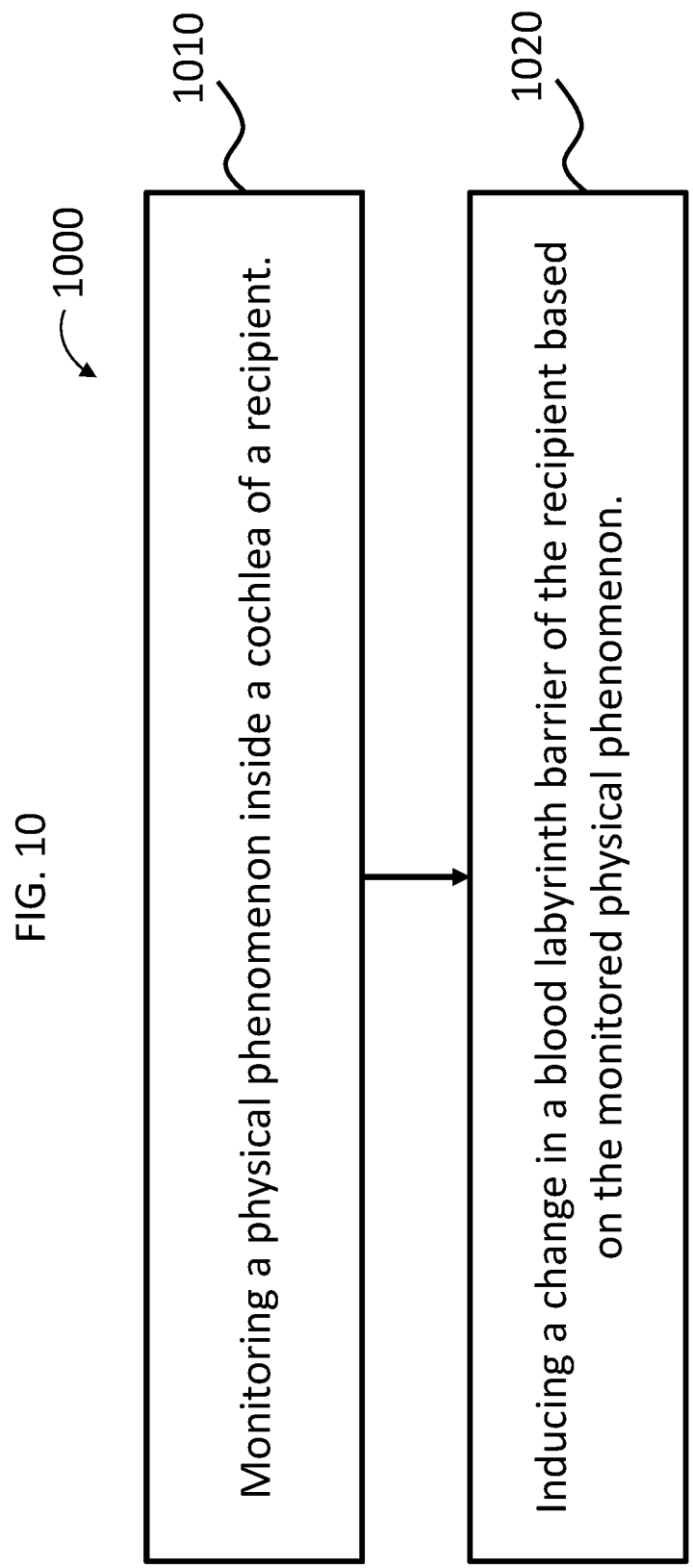
FIGS. 10-13 present exemplary algorithms for exemplary methods according to some exemplary embodiments.

In at least some exemplary embodiments, the teachings detailed herein associated with causing the trauma and/or inducing foreign body response are directed towards changing a blood labyrinth barrier of the recipient. In an exemplary embodiment, there is an exemplary method 1000, such as represented by the algorithm presented in FIG. 10, which includes method action 1010, which includes monitoring a physical phenomenon inside a cochlea of a recipient. In an exemplary embodiment, this action of monitoring can be executed utilizing the device detailed above, such as the pressure receptor, the temperature receptor, etc. To be clear, this can be executed using a measurement of the phenomenon by a probe outside of the cochlea—it is the location of the phenomenon that is addressed. In some embodiments, such is executed by measurement of the cochlea health from the round window niche, or other extra cochlear locations, as well as intra cochlear locations. Thus, in an exemplary embodiment, there is an implantable device that is configured to detect a physical phenomenon inside a cochlea by monitoring at a round window niche of the recipient and then open a tight junction of the cells at the round window upon the detection of the physical phenomenon. In an exemplary embodiment, a method of using such a device can include implementing the device to achieve the just described functionality and then deliver therapeutic substance at the opened junction.

Any location from which the phenomenon inside the cochlea can be monitored can be used and other extracochlear locations. Also, note that claim 1010 also includes the use of latent variables. For example, which are outside the cochlea associated with the physical, not inside the cochlea. In an exemplary embodiment, there can be a device that captures or otherwise is in contact with or otherwise directly exposed with fluid inside the cochlea and can analyze that fluid to determine whether or not a physical phenomenon inside the cochlea of a recipient's presence or otherwise has changed. The physical phenomenon can be any phenomenon indicative of a deleterious occurrence inside the cochlea, such as an infection resulting from the insertion of the cochlear implant, or such as a response to chemotherapy that causes the tissue of the inner ear to be damaged. Indeed, the physical phenomenon can be the presence of the chemotherapy substance. In an exemplary embodiment of such can be platinum-based chemotherapy, which, in some instances, is liable to cause the loss of hearing.

Method 1000 further includes the action of method action 1020, which includes inducing a change in the blood labyrinth barrier of the recipient based on the monitored physical phenomenon. In this regard, in an exemplary embodiment, the blood labyrinth barrier can control or otherwise influence the amount of a chemical substance that enters the inner ear or otherwise reaches the auditory system of the recipient when introduced outside of the auditory system. With reference to the chemotherapy example, in an exemplary embodiment, there is utilitarian value with preventing or otherwise reducing the amount of the chemicals of the chemotherapy from reaching the auditory system in general, and the inner ear and/or the middle ear specifically. Accordingly, by changing the blood labyrinth barrier, the amount of chemical that reaches the auditory system could potentially be reduced relative to that which would be the case in the absence of the change. Thus, in an exemplary embodiment, the physical phenomenon is a phenomenon correlated to ototoxicity. In an exemplary embodiment, trauma and/or the induction of a foreign body response can be such that changes the blood labyrinth barrier. By way of example only and not by way of limitation, causing trauma inside the inner ear can result in the blood labyrinth barrier becoming more "porous" such that the amounts of the chemical that is utilized for the chemotherapy that accumulates in the inner ear or in the auditory system is reduced relative to that which would be the case in the absence of the change in the blood labyrinth barrier. That is, in some embodiments, by making the barrier more porous, the outflow of the chemical will be increased relative to that which would otherwise be the case. That said, in some alternate embodiments, there is utilitarian value with respect to maintaining the blood labyrinth barrier so that the amount of chemical that reaches the inner ear is limited in a manner beyond controlling the accumulation in the first instance. That is, instead of opening up the barrier so as to flush the inner ear, the barrier is utilized to prevent the accumulation. This can correspond to changing the blood labyrinth barrier so that the porosity of the barrier is actually decreased relative to that which would be the case in the absence of the change.

In an exemplary embodiment, the adjustment of the BLB can increase or decrease a rate of substance transfer from inside the structure to outside the structure relative to that which would be the case in the absence of the adjustment in an exemplary embodiment, the rate is increased by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 350, 400, 450, 500, 550, 600, 650, 700, 750, 800, 900, 1000, 1100, 1200, 1300, 1400, 1500, 1600, 1700, 1800, 1900, 2000, 2500, 3000, 3500, 4000, 4500, 5000, 5500, 6000, 7000, 8000, 9000, or 10000 percent or more. In an exemplary embodiment, the rate is decreased by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 86, 87, 88, 89, 90, 91, 92, 93, 94, 95, 96, 97, 98, 99% or 100%.

In view of the above, it can be understood that in an exemplary embodiment, the change in the blood labyrinth barrier is an increase in the permeability thereof, and an amount and/or concentration of a substance in the cochlea is reduced due to the increase in the permeability relative to that which would be the case in the absence of the increase. More specifically, consistent with the chemotherapy scenario, in an exemplary embodiment, the substance is a drug introduced into the body of the recipient at a location away from the cochlea and is a drug unrelated to a hearing ailment. By way of example only and not by way of limitation, the substance can be a drug that is introduced into the arm or the groin of the recipient. In an exemplary embodiment, the substance can be a drug that is introduced into the mouth of the recipient such as by taking a pill or the like. In an exemplary embodiment, the substance can be a drug that is introduced through the nose of the recipient, such as something that is inhaled (like the thing used in Dawn of the Planet of the Apes).

It is also noted that the features of method 1000 can be applied in an alternate embodiment not associated with the cochlea, but instead, for example, in an embodiment associated with, for example, the kidneys. In this regard, the method of claim 1000 can be modified to monitor a physical phenomenon inside the kidney with respect to the scenario of managing or otherwise reducing the occurrence of aminoglycoside toxicity. Indeed, in an exemplary embodiment, the teachings detailed herein can be utilized with respect to a bionic eyes/retinal implant. In this regard, instead of an electrode array associated with a cochlear implant, the electrode array is associated with a retinal implant, and the associated devices detailed herein are associated there with and modified for use in or around the eye of the recipient.

It is noted that while the above embodiments have focused on the substance being a drug, in an alternate embodiment, the substance can be another type of substance other than a drug.

Conversely, in an exemplary embodiment, the change in the blood labyrinth barrier can be an increase in the permeability thereof, and the amount and/or concentration of the substance in the cochlea is increased due to the increase in the permeability relative to that which would be the case in the absence of the increase in permeability. By way of example only and not by way of limitation, in an exemplary embodiment, such as where the recipient is provided an oral drug that is configured to control infection or otherwise treat infection in the cochlea associated with the implantation of a cochlear implant, in an exemplary embodiment, by increasing the permeability of the barrier, more of that drug can reach the cochlea/inner ear/auditory system of the recipient, and thus can be more effective relative to that which would be the case in the absence of the adjustment of the barrier, all other things being equal (e.g., amount of drug be taken in the first instance, height, weight, size, metabolism of the recipient, etc.).

In an exemplary embodiment, the substance is a drug introduced into the body of the recipient at a location away from the cochlea and is a drug relating to a hearing ailment/ is a drug related to treatment of a hearing system of the recipient. That said, with respect to the chemotherapy example or the like, in an exemplary embodiment, the drug is a drug unrelated to a hearing ailment. Still further, in an exemplary embodiment, such as with respect to the kidneys, the drug can be a drug that is unrelated to a kidney ailment. In an exemplary embodiment where the teachings herein are directed towards and eye, the drug can be a drug that is unrelated to and eye aliment. Of course, where the teachings detailed herein are applicable to the aforementioned physical structures of the recipient, the drugs or substances etc. can be related to those structures.

The above embodiments have been directed towards increasing the permeability of the blood labyrinth barrier. In some embodiments, the methods are directed towards decreasing the permeability of the blood labyrinth barrier. Accordingly, in an exemplary embodiment, method action 1020 results in a decrease in the permeability of the barrier. In an exemplary embodiment of such, the amount and/or concentration of the substance in the cochlea is increased due to the decrease in the permeability relative to that which would be the case in the absence of the decrease in permeability. In an exemplary embodiment, in a scenario where the substance is a drug that is introduced into the body of the system at a location inside the cochlea, reducing the permeability (or, at least in some embodiments, preventing the permeability from increasing or at least limiting the increase of the permeability relative to that which would otherwise be the case in the absence of taking actions detailed herein—any disclosure herein of reducing the permeability of the BLB corresponds to a disclosure of the other two unless otherwise noted) of the BLB can have utilitarian value in a scenario where the substance is a drug that is introduced into the body of the system at the location inside the cochlea and/or proximate the cochlea. In an exemplary embodiment, there is a method action of stopping active stimulation for hearing and/or increasing the active stimulation for hearing (including activating such) to influence the leakage associated with the BLB (e.g., in some instances, the stimulation can cause a leaky BLB, and in other instances, the absence of stimulation can cause a leaky BLB). Also, closing the BLB/tightening up the BLB can, in some instances, decrease the elimination of a drug and/or increase its half-life thereby allowing it to diffuse further toward the apex. Conversely, in some embodiments, controlling the BLB can be utilized to target specific locations for example, if we only want to treat the base, the opposite of the aforementioned embodiment can apply, where the barrier is opened up to limit how far apically up the cochlea the drug or otherwise therapeutic substance can diffuse.

By way of example only and not by way of limitation, a therapeutic drug, such as an anti-rejection drug, can be delivered via the electrode array, such as with the embodiment of FIG. 9, or such as with the embodiment of FIG. 8, which delivers the therapeutic substance outside the cochlea but which therapeutic substances diffused through the wall of the cochlea to inside the cochlea, and thus is delivered at a location proximal the cochlea. This therapeutic drug can be a drug where there is utilitarian value with respect to preventing at least some of the drug from leaching or otherwise diffusing or otherwise leaving the cochlea. That is, this can be a drug where there is therapeutic value with respect to maintaining a concentration and/or an amount in the cochlea at a higher level than that which would be the case if the drug was permitted to escape from the cochlea. Accordingly, the change in the blood labyrinth barrier that decreases the BLB could limit the amount of therapeutic substance that escapes from the cochlea relative to that which would be the case in the absence of such change, all other things being equal. That said, in an exemplary embodiment, simply preventing the BLB from becoming more permeable or even limiting the amount of increase of permeability can also have utilitarian value, such as, for example, the preservation of residual hearing.

Figure 11:
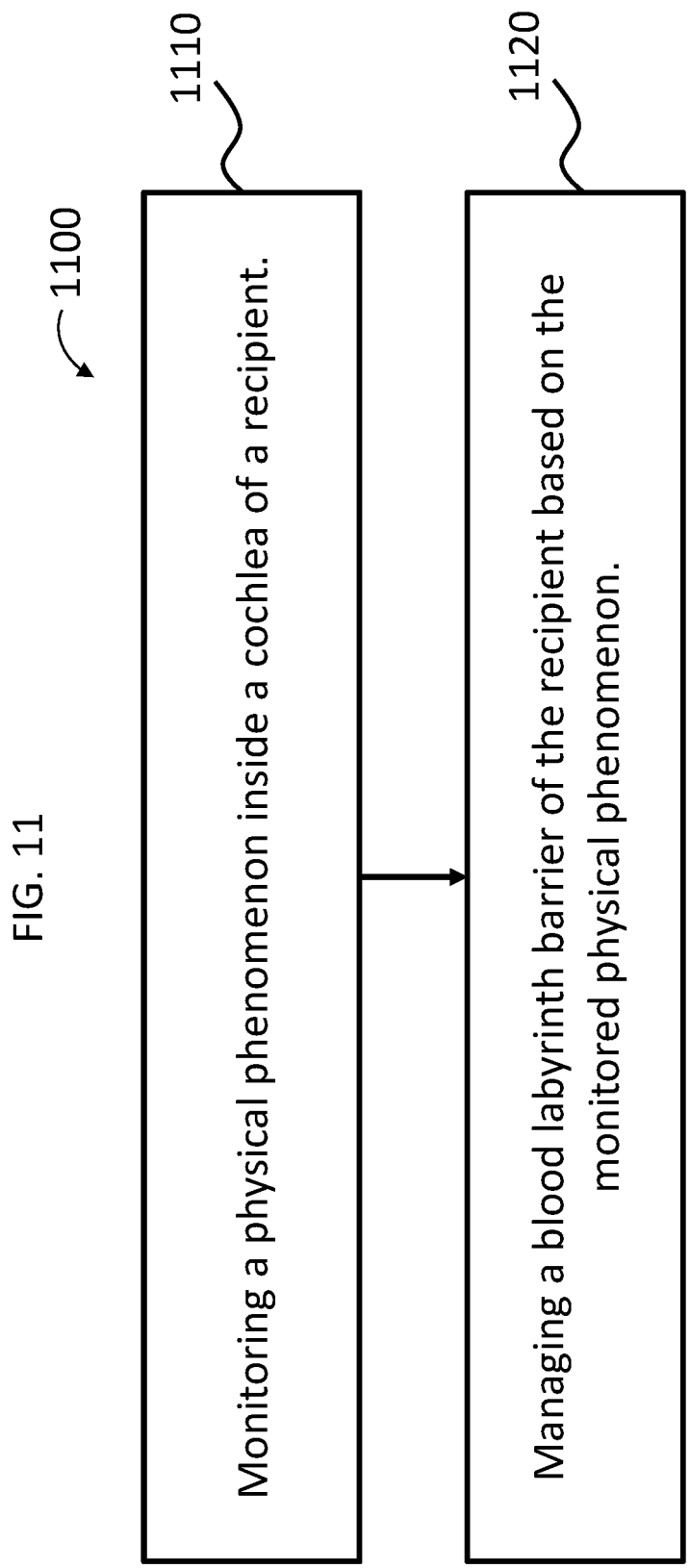

FIG. 11 provides another exemplary method, method 1100, which includes method action 1110, which corresponds to method action 1010 detailed above. Method 1100 also includes method action 1120, which includes the action of managing a BLB of the recipient based on the monitored physical phenomenon. In this regard, the management can include increasing the permeability, limiting a decrease in the permeability relative to that which would be the case in the absence of the management or preventing a decrease in the permeability. It is noted that in at least some exemplary embodiments detailed herein, any disclosure herein of increasing the permeability corresponds to a disclosure of the other two unless otherwise specified. Also, management can include decreasing the permeability, limiting an increase in the permeability relative to that which would be the case in the absence of the management, or preventing an increase in the permeability. It is noted that in at least some exemplary embodiments detailed herein, any disclosure herein of decreasing the permeability corresponds to a disclosure of the other two unless otherwise specified.

It is noted that in at least some exemplary embodiments, the action of increasing the permeability of the BLB can be achieved by introducing trauma and/or otherwise eliciting a foreign body response, or otherwise providing an irritant to tissue. In an exemplary embodiment, the action of decreasing the permeability of the BLB can be achieved, in some embodiments, by removing that trauma or otherwise mitigating that trauma or otherwise removing the resulting foreign body response or otherwise mitigating that form body response or otherwise removing the irritant from the tissue. In an exemplary embodiment, this can be executed by the application of an active chemical to mitigate the trauma, where the application of any other therapeutic or otherwise useful substance to mitigate the trauma, all at least in part.

Any disclosure of increasing an amount and/or concentration of a substance due to the management also corresponds to a disclosure of preventing a decrease in the amount and/or concentration or limiting a decrease in the amounts and/or concentration relative to that which would be the case in the absence of the management. Also, any disclosure of a decrease in the amount and/or concentration of a substance due to the management also corresponds to a disclosure of preventing an increase in the amount and/or concentration where limiting an increase in the amounts and/or concentration relative to that which would be the case in the absence of the management.

It is noted that the action of inducing the change or otherwise managing the BLB of the recipient can be executed via the injection of an inflammatory and/or an anti-inflammatory compound to a scala tympani of the cochlea. In an exemplary embodiment, this can be executed utilizing an exemplary embodiment of the device detailed above, such as the device of FIG. 9. In an exemplary embodiment, this can be done manually utilizing a needle or the like/syringe assembly or the like. This can be done, for example, during the surgery implanting the cochlear implant or other hearing prosthesis.

Figure 12:
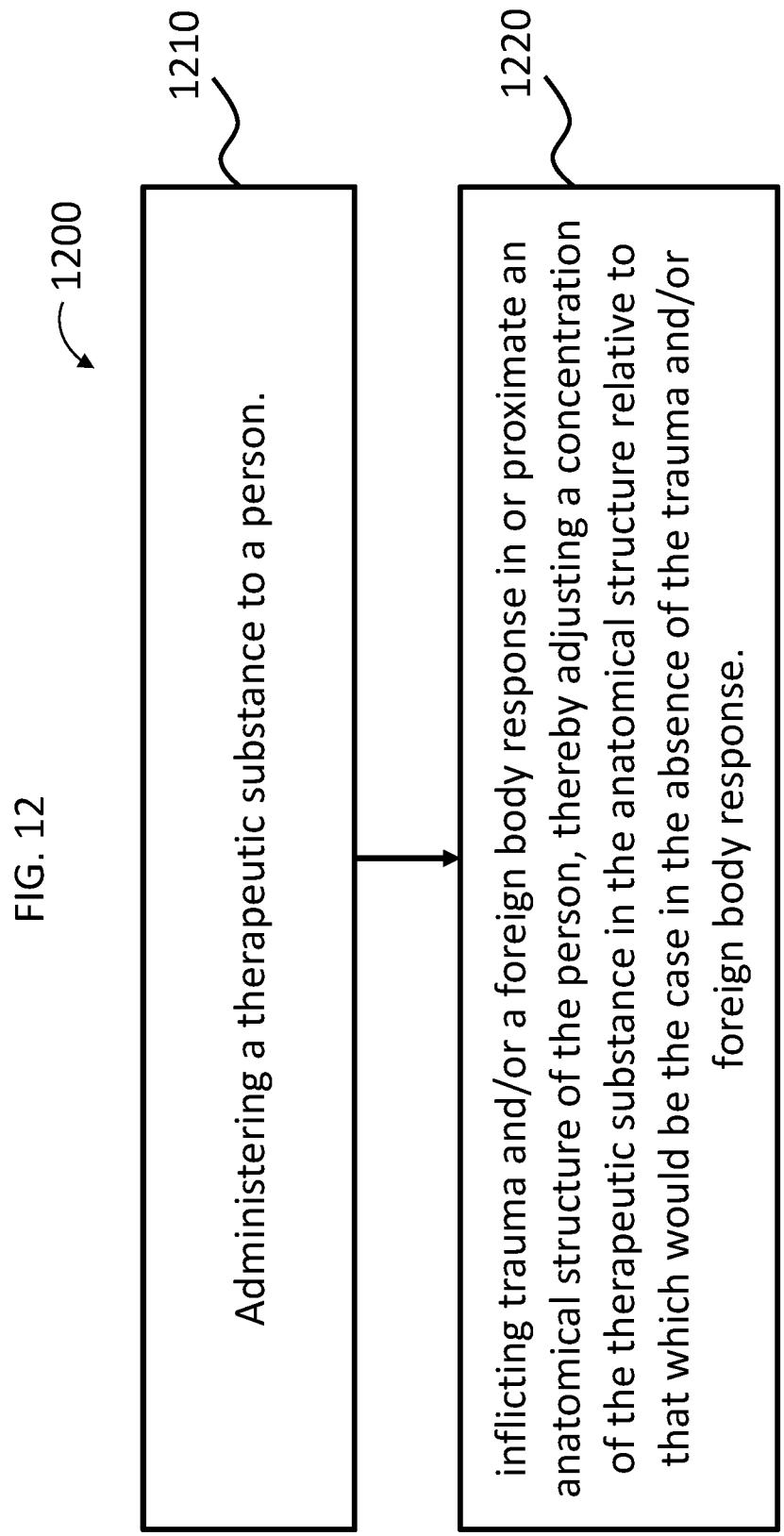

FIG. 12 presents an exemplary algorithm for an exemplary method, method 1200, which includes method action 1210, which includes the action of administrating a therapeutic substance to a person. This can be done according to any of the teachings detailed herein, such as intravenously, orally, etc. This can be done utilizing a combined drug delivery system and prostheses. This can be done using a separate drug delivery system that is implantable that is separate from the prosthesis. This can be done at or proximate the body structure at issue or can be done remotely there from.

Method 1200 also includes method action 1220, which includes inflicting trauma and/or inducing a foreign body response in or proximate an anatomical structure of the person, thereby adjusting a concentration and/or amount of the therapeutic substance in the anatomical structure relative to that which would be the case in the absence of the trauma and/or foreign body response.

In an embodiment, the adjustment is a reduction or increase in an amount and/or concentration of therapeutic substance in the anatomical structure relative to that which would be the case in the absence of the trauma and/or foreign body response. In an exemplary embodiment, the increase results in an increase of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 350, 400, 450, 500, 550, 600, 650, 700, 750, 800, 900, 1000, 1100, 1200, 1300, 1400, 1500, 1600, 1700, 1800, 1900, 2000, 2500, 3000, 3500, 4000, 4500, 5000, 5500, 6000, 7000, 8000, 9000, or 10000 percent or more. In an exemplary embodiment, the decrease results in a decrease of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100%.

In an exemplary embodiment, the anatomical structure can be a cochlea, a kidney, an eye, a heart valve, etc.

In an exemplary embodiment, the anatomical structure can be a cochlea, and the person is a recipient of a cochlear implant that includes an electrode array inserted into the cochlea. Consistent with the embodiment of FIG. 3 or FIG. 8, the cochlear implant is the device that inflicts the trauma and/or induces the foreign body response.

The teachings detailed herein can be combined with a smart system or the like so as to work with the recipient to enhance a drug delivery regime. By way of example only, and not by way of limitation, an exemplary embodiment can entail the intentional driving of inflammation in the cochlea by electrical stimulation, via the existing electrodes or via other electrodes, or via other systems, such as an optical electrode, etc. The drug could then be systematically delivered orally and/or via an intravenous injection, and the drug would be able to better reach the cochlea relative to that which would be the case in the absence of the aforementioned driven inflammation. The inflammation can be achieved by inflicting the trauma and/or inducing the foreign body response. In an exemplary embodiment, the protocol could be executed with the assistance or otherwise with the interaction of the recipient. By way of example only and not by way of limitation, a reminder such as a daily or weekly or monthly or hourly or multi-hour reminder etc., could be provided to the recipient, such as an automated reminder to take a pill at a time. At some time later, minutes, hours, maybe even days, the smart device could ask the recipient whether or not he or she has taken the pill, and if the answer is yes, then initiate the trauma and/or the foreign body response. In an exemplary embodiment, the recipient could instead input the time at which he or she took the pill, and then the smart device would initiate a timed countdown where the end of which would result the inflection of the trauma and/or the foreign body response utilizing the implanted device. In an exemplary embodiment, the smart device is the prosthesis. In an exemplary embodiment, the prosthesis can provide an artificially evoke a hearing percept that asks the question "did you take your pill" or the like. Upon a yes indication, which could simply be the recipient stating yes, where the prosthesis is configured to analyze captured sound and can analyze that as an affirmative answer, or in an alternate embodiment, the input to the prostheses would be via a smart phone or a smart device or even a dumb device or a remote assistant, or via a button on the prosthesis, such as a button on the earpiece or the like.

Figure 13:
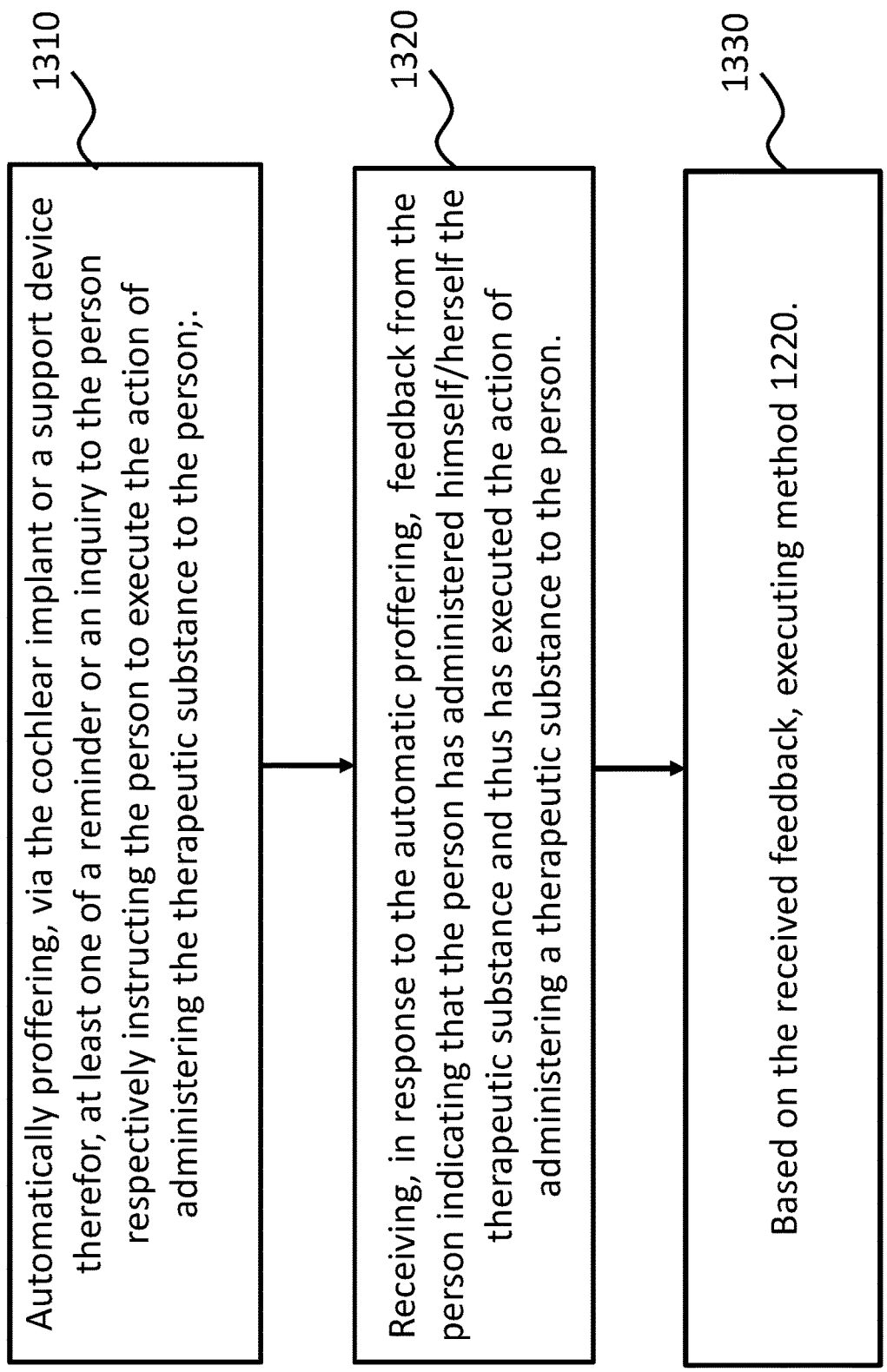

In view of the above, FIG. 13 presents an exemplary method, method 1300, which includes an algorithm according to an exemplary embodiment. Method 1300 includes method action 1310, which includes automatically proffering, via the cochlear implant and/or a support device, such as a smartphone as seen in FIG. 14, therefor, at least one of a reminder or an inquiry to the person respectively instructing the person to execute the action of administering the therapeutic substance to the person (which could be taking a pill.)

Method 1300 also includes method action 1320, which includes receiving, in response to the automatic proffering, feedback from the person indicating that the person has administered himself/herself the therapeutic substance and thus has executed the action of administering a therapeutic substance to the person (of method 1200).

Method 1300 also includes, based on the received feedback, inflicting the trauma and/or the foreign body response using the cochlear implant, corresponding to method action 1220.

Figure 14:
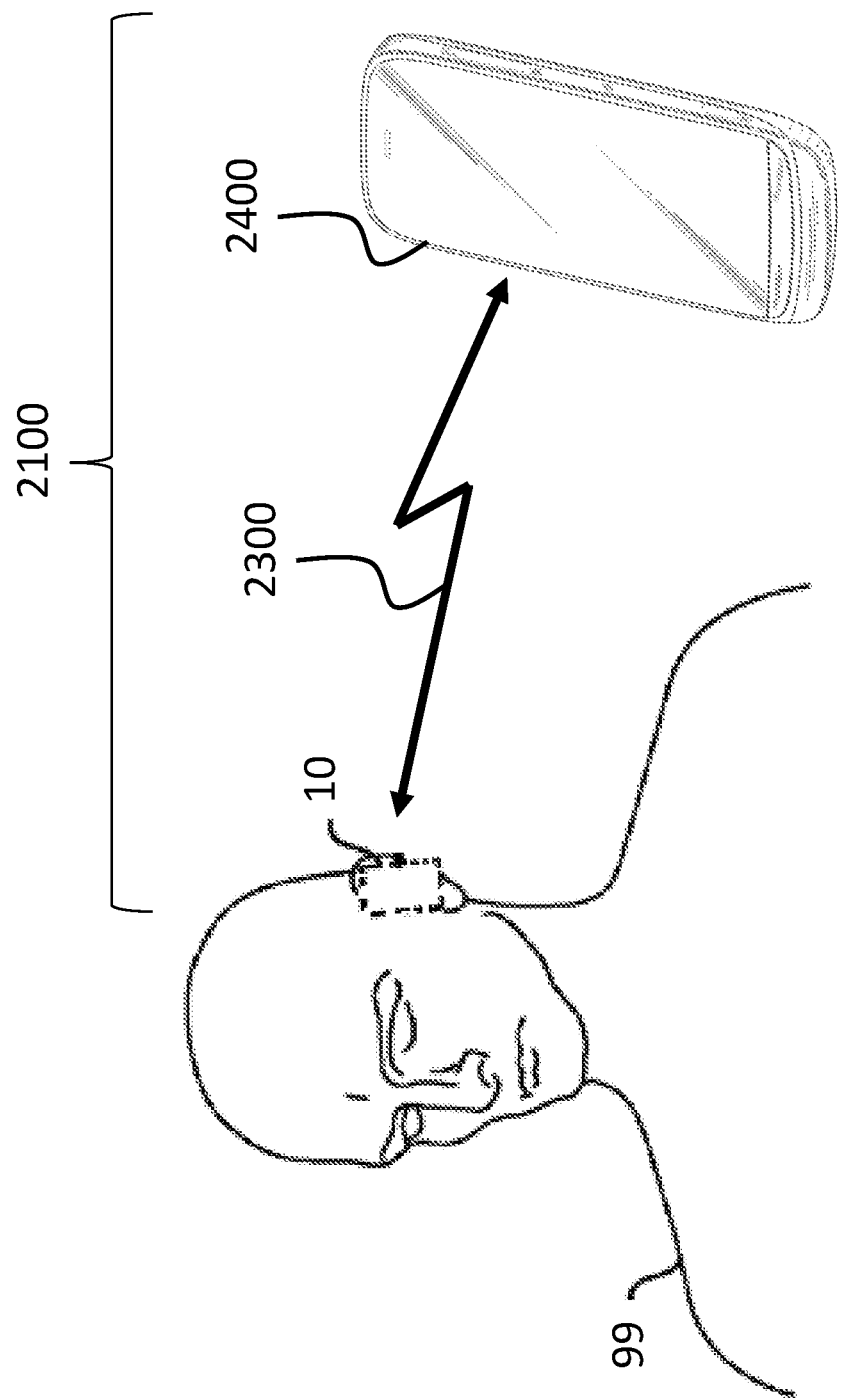
FIG. 14 presents an exemplary system according to exemplary embodiment.

FIG. 14 presents an exemplary system, system 2100, which can be utilized in an exemplary embodiment of executing method 1300, or any of the other methods detailed herein where there is input or otherwise a controller associated there with. System 2100 includes the prosthesis 100, which is attached to the recipient 99, and is in signal communication via wireless link 2300, with smart phone 2400. It is noted that in some exemplary embodiments, instead of a wireless link, a wired link can be utilized. In such exemplary embodiments, there can be utilitarian value with respect thereto in view of the fact that it is impossible for an extraneous signal in the RF spectrum to initiate one or more the actions detailed herein. Put another way, only something that is hardwired with the smart phone 2400 can be utilized to control the prosthesis. In an exemplary embodiment, the prosthesis 10 is a cochlear implant. That said, in an exemplary embodiment, the prosthesis can be another of the devices detailed herein, such as the dedicated drug delivery and/or the dedicated trauma inducing/foreign body response eliciting devices detailed herein and/or variations thereof. In an exemplary embodiment, the smart phone 2400 can provide the indicators of the method 1300, such as by presenting such in a text message one the screen thereof, or by an audio system. In an exemplary embodiment, the smart phone 2400 utilize input from the recipient according to the input associated with method 1300. While the embodiment of FIG. 14 presents the utilization of a smart phone 2400, in an alternate embodiment, element 2400 need not be a smart device. Element 2400 can be a dumb device, or a device that is a remote assistant with the prosthesis. Any device, system, and/or method that can enable one or more the teachings detailed herein can be utilized in at least some exemplary embodiments.

It is noted that in at least some exemplary embodiments, the action of inflicting trauma and/or the foreign body response is executed by applying an irritant to the structure of the person. In an exemplary embodiment, this can be a mechanical irritant, such as the balloons/inflated membranes of FIG. 3A. In an exemplary embodiment, this can be a chemical irritant. In an exemplary embodiment, the drug delivery devices detailed above and/or variations thereof can be utilized to deliver the irritant. That said, in an exemplary embodiment, devices of FIGS. 3A and 7 can be modified to provide the irritant. By way of example only and not by way of limitation, a chemical irritants can be provided on the surface of the balloons, which, when the balloons are inflated, and thus contact the wall of the cochlea, the chemical interacts with the wall of the cochlea to result in the trauma. The device of FIG. 7 can be utilized to exude a chemical irritants on to the round and/or oval walls of the cochlea or otherwise on to the wall/barrier between the middle ear and the inner ear.

In an exemplary embodiment, irritant can be a sonic irritant, such as an ultrasonic device. In an exemplary embodiment, the irritant can be a surface that is structured to cause irritation. While the embodiments detailed above utilizing moving components of focused on an active trauma inducing device, in an exemplary embodiment, the prosthesis detailed herein can be more of a passive arrangement. In this regard, in an exemplary embodiment, a surface or the like can be extended to contact tissue of the recipient, but after that, nothing else occurs vis-à-vis movement of the surface via an active action. Instead, the normal movements of the recipient can be utilized to induce the irritation, such as by way of example, that which results from a grain of sand in an oyster. For example, in an exemplary embodiment, the balloon of FIG. 3A could simply expand to contact the wall, and remained expanded. As the recipient moves, or indeed, as the recipient is subjected to sounds, the waves of fluid motion could move the balloons in a manner that causes the irritation. Instead of balloons, a mechanical device can extend out to contact the cell walls, such as, for example, a telescoping component that extends in a direction orthogonal or at an angle that is acute to the longitudinal direction (local) of the array so as to place a service that will result in irritation against the wall of the cochlea. In an exemplary embodiment, this can be a spring-loaded device. Indeed, in an exemplary embodiment, a magnetorestrictive material can be utilized, which material controllably deforms would subjected to an electric current or the like so as to variously come into contact with the tissue and then retract from contact with the tissue. In some embodiments, a motor or the like can be utilized to move a structure actually about the electrode array. By way of example only and not by way of limitation, a series of wire like structures can extend actually away from the longitudinal axis of the array, which can be supported when a ring or the like. A motor can spin the ring, however so slowly or fastly, which thus moves the wires. As the wires scrape or otherwise move along the wall of the cochlea, the wires can cause a modicum of trauma or otherwise induce a foreign body response. Indeed, such an exemplary embodiment can have utilitarian value with respect to also positioning the cochlear implant electrode array in place. It is noted that in at least some exemplary embodiments, spikes or the like are utilized to puncture at least a portion of the wall of a given structure. Such can result in trauma and/or the initiation of the foreign body response. Indeed, in an exemplary embodiment, a device akin to a splinter can be utilized, which splinter, when piercing the outer wall of the tissue, evokes a foreign body response.

Again, optical electrodes can be utilized. In some embodiments, heat can be utilized. In this regard, a heating device can be utilized that applies thermal energy to the tissue structure. In some embodiments, cold can be utilized. In this regard, a device that extracts thermal energy from the tissue structure can be utilized. Any device, system, and/or method that can enable the trauma and/or the introduction of the foreign body response or otherwise that can cause the irritation so as to manage the BLB can be utilized at least some other embodiments.

In an exemplary embodiment, the irritants that are utilized can be an irritant that inflames the blood labyrinth barrier.

Consistent with the teachings detailed above, irritant can be applied to a structure of the cochlea and door of the middle ear. In an exemplary embodiment, the action of administering the therapeutic substance to the person is executed by administering the substance at a location remote from the structure. That said, in an exemplary embodiment, the action of administrating the therapeutic substance to the person is executed by administering that substance at a location proximate or at the structure.

It is noted that the embodiments detailed above have in many instances focused on the utilization of a prosthesis that provides the trauma/induces the foreign body response, or otherwise results in the irritation. In an exemplary embodiment, a manual device/non-prosthetic device can be utilized. For example, a needle that is handheld and be utilized to induce the trauma. In an exemplary embodiment, the chemical irritant can be applied utilizing a range of the like, again manually operated. In an exemplary embodiment, in irritant can be delivered to the round window and/or the oval window, during a surgery, by the surgeon. Of course, this could also be done or alternatively done by the prostheses after implantation. This could result in a mildly irritated BLB, and thus a mildly or even more than mildly open BLB.

After this, therapeutic substances could be delivered in a systematic run on systematic manner. These can be provided orally, intravenously, or locally during the surgery, or can be delivered via a device that implanted in the recipient. Such can result in the achievement of higher concentrations and/or higher amounts of the therapeutic substances at the local location. This can be performed in a one-hit delivery, this can be done in a manner that is time to the irritation of the BLB to achieve a one-off dose, or can be achieved in a more systematic manner to maintain the increased concentrations and/or the higher amounts of the substances, relative to that which would be the case in the absence of the teachings detailed herein.

Still, it is noted that at least some exemplary embodiments detailed above have focused on the implantable devices. Accordingly, in an exemplary embodiment, there is a system comprising an implantable blood labyrinth barrier management component configured to influence the blood labyrinth barrier to control an amount of a substance in an anatomical structure beyond that which would be the case in the absence of the influence. In the exemplary embodiments detailed above, such a system can be that of FIG. 7, etc. Any arrangement that can influence the BLB can be utilized in at least some exemplary embodiments. The system need not have associated there with an implantable sensory prosthesis. That said, in alternative embodiments, consistent with the teachings detailed above, the system can include an implanted sensory prostheses. Such an embodiment can correspond to, for example, the embodiment of FIG. 3A or FIG. 8 or 9, etc. Consistent with these embodiments, in an exemplary embodiment, there is an implantable sensory prosthesis component that is part of the system, wherein the blood labyrinth barrier management component is integrated with the sensory prosthesis component. Conversely, in some embodiments, the blood labyrinth barrier management component can be utilized separately and can be a separate component from the sense prostheses. For example, the embodiment of FIG. 7 can be utilized with the embodiment of FIG. 1. RF inductance coil's implanted in the recipient can be implanted next to each other so that the components can be utilized separately. That said, utilizing two separate external components, the components can be utilized at the same time.

It is also noted that while some of the embodiments detailed above have been directed towards devices that combine the BLB management component with the sensory prosthesis, in some embodiments, the BLB management component can instead or also be part of an implantable drug delivery component, wherein the drug delivery component is configured to deliver the substance to the anatomical structure. Indeed, in an exemplary embodiment, the implantable component is configured to measure or otherwise evaluate a concentration and/or an amount of a drug or some other substance or other some phenomenon having correlation thereto, at a local location, and effectively open and/or close the BLB to achieve a desired concentration and/or an amount in substance, or otherwise very or otherwise influence the amounts and/or concentrations of the therapeutic substance. In an exemplary embodiment, that there can be method actions that include a loop delivery, such as a regime that includes delivery/opening/delivery/opening/delivery/opening/delivery/opening, and so on, to achieve a therapeutic goal. In some instances, this loop can be executed in a fashion that precisely modulates the inner ear drug concentration by increasing and/or reducing concentration as is utilitarian. Indeed, in an exemplary embodiment, the loop can include delivery/opening/delivery/opening/closing/delivery/opening/opening more/closing/delivery/opening, etc. In this regard, the actions of opening and/or closing can be executed repeatedly as utilitarian to achieve a level of precision beyond that which would be the case by simply executing one or more the method actions once. In an exemplary embodiment, the cochlear implant can be utilized to potentially regulate, in a closed loop feedback, the therapeutic substance in or proximate the cochlea. In an exemplary embodiment, the cochlear implant can be utilized to potentially regulate, in a closed loop feedback, the deleterious substance in our proximate to the cochlea.

Figure 15:
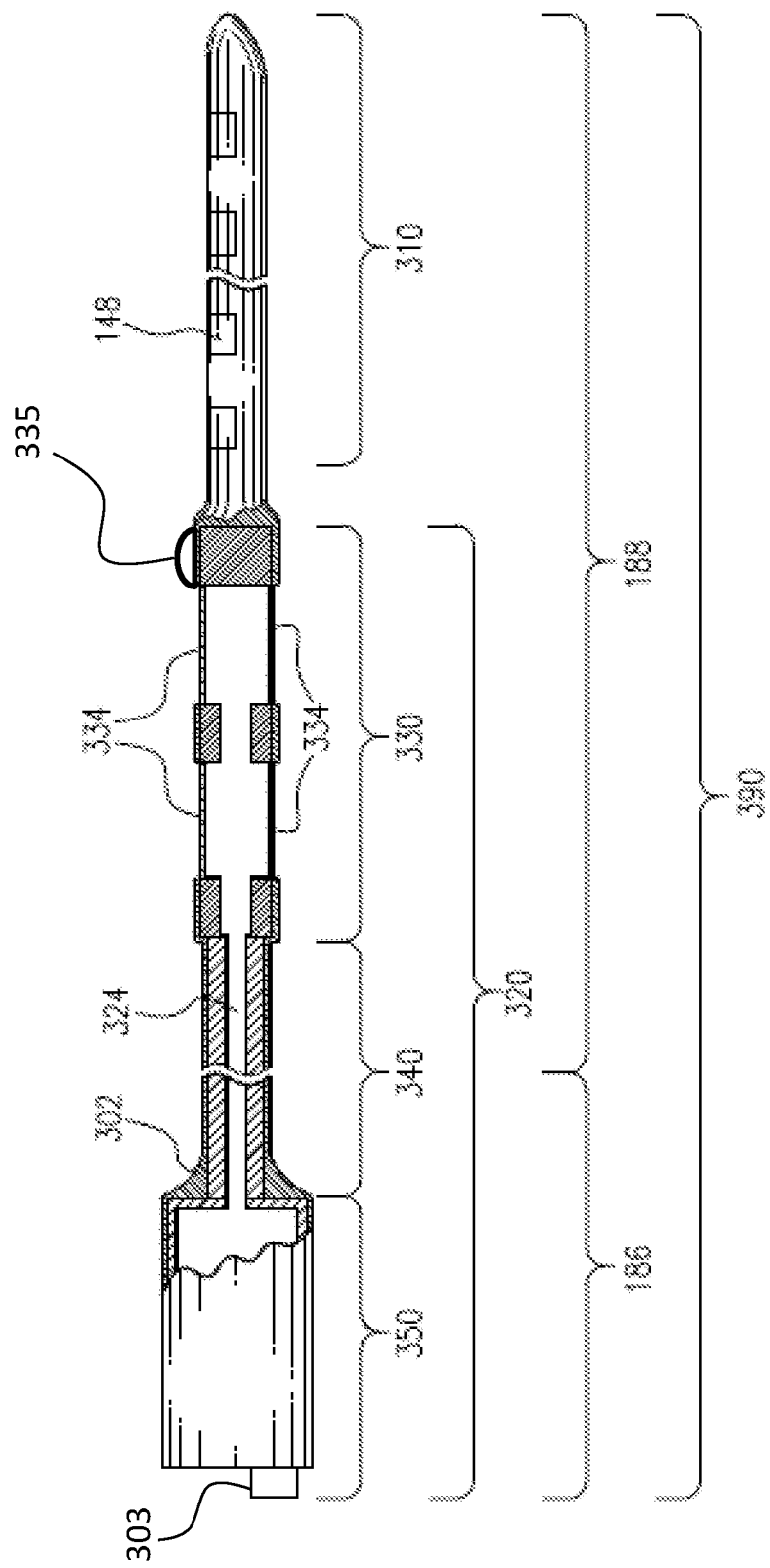
FIG. 15 presents an alternate exemplary embodiments of the exemplary embodiment of FIG. 3A.

In this regard, in an exemplary embodiment, as seen in FIG. 15, there can be a sensor 335 that is part of the sensory prosthesis (or part of the drug delivery system, or part of the trauma inducing and/or the foreign body response eliciting device, etc.), that is located such that when the prostheses is implanted in the recipient, the sensor 335 can be located at the location where a concentration and/or an amounts of the substance at issue can be or otherwise is desired to be monitored or otherwise regulated or managed. In this regard, in an exemplary embodiment, the sensor 335 be a chemical sensor and/or a mass sensor and/or a particulate sensor, which is in wired or wireless communication with another component of the prostheses, and can be integrated or otherwise in signal communication with a controller or the like, such as a processor that is programmed to execute one or more the teachings detailed herein, which process can be programmed to analyze the signal from the sensor 335 and evaluate the amounts and/or concentration of the substance at issue. Based on the evaluation, the prostheses can be controlled so as to manage the BLB in accordance with the teachings detailed herein so as to adjust or maintain the BLB in a manner so that the amounts and/or concentrations of the substance at issue that is desired is achieved or otherwise maintained or otherwise the amounts and/or concentrations of the substance at issue are pushed towards the desired quantities.

As with some of the embodiments detailed above, in an exemplary embodiment, the blood labyrinth barrier management component can be configured to deliver an inflammatory substance to or proximate to the anatomical structure.

In an exemplary embodiment, the blood labyrinth barrier management component is configured to at least passively manage the blood labyrinth barrier, while in other embodiments, the blood labyrinth barrier management component is configured to at least actively manage the barrier. It is noted that the two are not exclusive, and that in some embodiments, the management component can both actively and passively manage the BLB.

In an exemplary embodiment, any disclosure herein of a foreign body response also corresponds to a disclosure of a foreign body response followed by encapsulation. In some embodiments, such can allow encouragement of inflammation for a period of time and then allow normal healing.

In view of the above, it can be seen that in at least some exemplary embodiments, there is a device and system that enables and a method that results or otherwise includes the utilization of an inflammatory compound or an inflammatory structure or an inflammatory action manage the BLB. In an exemplary embodiment, the inflammatory compound is delivered to the middle ear and/or localized to the round window and/or the oval window. In an exemplary embodiment, the methods detailed herein can include the utilization of an inflammatory compound delivered from the cochlear implant and/or from a drug pump and/or from a middle ear implant/direct acoustic cochlear stimulator. In some exemplary embodiments, an implant can be placed into the recipient, which implant has, as its primary purpose, and in at least some exemplary embodiments, it is only purpose, as being an implant that elicits a foreign body response and/or induces trauma and/or results in the aforementioned irritations, which can manage the BLB, such as by opening the BLB and/or closing the BLB. The elicitation of the foreign body response, etc., can be done by an active arrangement and/or by a passive arrangement.

To be clear, the inflammatory compounds and/or the irritating actions and/or the trauma inducing actions and/or the foreign body eliciting actions can be executed by utilizing a prosthesis and/or can be executed in a manual manner. Indeed, in an exemplary embodiment, a splinter or the like can be implanted by the surgeon in the cochlea or in the round wall or the like, which splinter can elicit a foreign body response. Electrical stimulation can be applied through the skin in some embodiments. In this regard, an electrode can be placed in the ear canal of the recipients during a checkup procedure.

Again, any device, system, and/or method that can enable the BLB to be managed can be utilized in at least some embodiments. This can entail, for example, the utilization of noise (audible noise), the utilization of ultrasound, the utilization of infra sound, and/or the utilization of pressure and/or the utilization of heat and/or cold. Any type of stimulation that can enable the BLB to be managed can be utilized in some embodiments. Indeed, if stimulation at a location remote from, for example, the cochlea can be utilized to manage the BLB, such can be done in some embodiments.

It is noted that in at least some exemplary embodiments, any one or more of the actions detailed herein not associated with evoking a hearing percept are executed in a manner that cannot be heard by the recipient. In this regard, in an exemplary embodiment, at least some of the actions herein are executed without evoking a hearing percept.

To be clear, in at least some exemplary embodiments, the barrier between the blood vessels and the neural tissue and/or functional structures and/or tissues of the organ at issue can be managed, such as by controlling inflammatory responses. The teachings detailed herein can be utilized, in at least some exemplary embodiments, to protect or otherwise reduce the likelihood that the neural nerve, which is very sensitive to chemotherapy or any other phenomenon, could be damaged or otherwise reduce the resulting damage there from via the management of the BLB, as a result of the occurrence of the given phenomenon. In some embodiments, the teachings detailed herein are utilized to limit entry of a toxin, and/or to limit entry of immune cells. In an exemplary embodiment, the teachings detailed herein are utilized to increase entry of therapeutic substances, such as a steroid that is delivered intravenously. In exemplary embodiments, the management of the BLB can be utilized to better approach a full treatment with a therapeutic substance, relative to that which would be the case in the absence of the teachings detailed herein.

The teachings detailed herein can be also utilized in some exemplary embodiments where the drugs are delivered at the time that the implantation of the sensory prosthesis is executed. In at least some scenarios, drug concentrations decrease after the implantation time, at least without the teachings detailed herein. The teachings detailed herein can be utilized so as to prevent that decrease or at least limit that decrease.

Various teachings above referred to the systemic delivery of substances. Various teachings above referred to the local delivery of substances (e.g., into the cochlea or to the wall of the cochlea or to the round or oval window, etc.). In at least some exemplary embodiments, the substances are therapeutic substances, such as drugs. In at least some exemplary embodiments, the substances that are delivered can be steroids.

The teachings detailed herein can be utilized to manage concentrations and/or amounts of substances that are delivered systemically and/or locally. The teachings herein can also be utilized to manage concentrations and/or amounts of substances that are delivered both systemically and locally. In this regard, in an exemplary embodiment, a substance can be delivered locally at the same time more relatively proximate the temporal manner to the substance being delivered systemically. In an exemplary embodiment, there is a method that includes balancing or otherwise manipulating or controlling or influencing a substance gradient within a structure of a recipient with the substance gradient outside the structure of the recipient. In this regard, in an exemplary embodiment, a low substance concentration in a structure, combined with management of the BLB, such as by opening the BLB or otherwise increasing the permeability of the BLB, can result in a systemically applied substance being drawn into the structure. This could be because, in some exemplary embodiments, the concentration in the structure is low and the systemic and/or blood concentration is high. Conversely, in an exemplary embodiment, a high substance concentration in a structure, with an open BLB, can result in a locally applied substance being dissipated. This could be because, for example, of a concentration gradient between the structure and the rest of the body. Thus, in view of the above example, it can be seen that in at least some exemplary scenarios, the systemic treatment is superior to the local treatment, which would seem to be counterintuitive. It is possible that in at least some exemplary scenarios as such, this counterintuitive result is due to the fact that the BLB is open. At least some exemplary embodiments include managing or otherwise controlling or otherwise balancing the substance delivered systemically with the substance delivered locally so as to achieve or otherwise manage the concentrations and/or amounts desired in the structure.

In view of the above, in an exemplary embodiment associated with a cochlea, a scenario can exist where the systemic delivery of a steroid is superior to that which would result from a local steroid administration, all other things being equal. In an exemplary embodiment, this can be because, the perilymph in the cochlea has no or little drug concentration but the blood labyrinth barrier is open. This can result in a concentration gradient that can draw the steroid into the cochlea, and thus into the perilymph, thus increasing the concentration and/or an amount therein relative to that which would be the case in the alternative local administration. It is noted that in at least some exemplary embodiments, these quantities are temporally based over periods of days or weeks or months. In an exemplary embodiment, the aforementioned differences or values or quantities are averaged over 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 350, 400, 450, 500, 550, 600, 650, 700, 750, 800, 900, 1000, 1100, 1200, 1300, 1400, 1500, 1600, 1700, 1800, 1900, 2000, 2500, 3000, 3500, 4000, 4500, 5000, 5500, 6000, 7000, 8000, 9000 or 10000 hours, or days. It is also noted that the differences or values or quantities can be measured and/or averaged after a set period of time has elapsed. By way of example only and not by way of limitation, in an exemplary embodiment, it will always be the case that a locally administered drug will have a higher concentration/higher amounts at the local area than that which would be the case with respect to systemic administration. But this phenomenon would exist only for a period of time. Accordingly, in an exemplary embodiment, the balancing where the evaluation can begin to take place after that period of superior performance would be diminished. In this regard, it can be assumed that for the first two or three or four days or hours or weeks etc., the locally administered drug will be superior. The management can then begin after that period of superiority. That said, in an alternate embodiment, the periods of superiority can be taken into account and utilize as part of the treatment regime. It is noted that the teachings detailed herein are not steroid dependent in some embodiments. In some instances, some or most or all drugs will have side effects. This method/approach may allow reduced systemic concentration of drugs.

Corollary to the above is that a locally administered drug can result in a high concentration of that drug in the perilymph, and with a BLB that is open, if there is a gradient that is high relative to the amounts of the substance outside the cochlea, the drug could be quickly lost from the cochlea. In this regard, it is noted that that period until the drug is lost from the cochlea can be the aforementioned superiority.

In view of the above, an exemplary embodiment can include tailoring a systemic dose and a local dose of a substance to achieve a desired amount and/or concentration, or otherwise drive the concentrations and the amounts towards the desired amount and/or concentration. By way of example only and not by way of limitation, for an exemplary drug, in some instances, it can be utilitarian to not apply any drug locally and instead apply the drug entirely systemically. Still further, for an exemplary drug, in some instances, it can be utilitarian to only apply that drug locally and not apply that drug systemically. Still further, by way of example, it can be utilitarian to apply that drug both locally and systemically utilizing various and different dosages for the two so that the concentrations within the structure and outside the structure, such as within the cochlea and outside the cochlea, are managed such that, combined with an open and/or a closed or partially closed BLB, the concentrations and/or amounts can be controlled. (While the embodiment herein has been directed towards the cochlea, it is noted that the teachings detailed herein can be applied to the hearing and balance organs as well, to the extent that they share common features applicable to the teachings detailed herein. Is also noted that the teachings detailed herein can be applied to the eye as well. Accordingly, any disclosure herein of treating organ or otherwise a method associated with such and/or a device for treating such corresponds to a disclosure of treating any of the aforementioned organs herein, including the eye, providing that the art enables such and that the specific teachings can be modified to accomplish such.)

In an exemplary embodiment, the amounts that are applied at the local location can range from zero to the highest amount possible or at least the highest amount where irrespective of what occurs, additional amounts will be wasted or otherwise not utilitarian, and the amounts that are applied systemically can range from the highest amount possible or at least the highest amount where irrespective of what occurs, and additional amounts will be wasted or potentially dangerous, to zero. By balancing the two amounts, a utilitarian treatment can be developed. The tables below provide exemplary conceptual unit amounts. In an exemplary embodiment, the application of a certain local amount combined with a certain systemic amount can, in some embodiments, yield a utilitarian result, such as for a given BLB status.

| Unit Local | Unit Systemic |
|---|---|
| 0 | 100 |
| 5 | 95 |
| 10 | 91 |
| 15 | 87 |
| 20 | 84 |
| 25 | 81 |
| 30 | 79 |

| Unit Local | Unit Systemic |
|---|---|
| 0 | 100 |
| 5 | 90 |
| 10 | 80 |
| 15 | 50 |
| 20 | 30 |
| 25 | 10 |
| 30 | 0 |

| Unit Local | Unit Systemic |
|---|---|
| 0 | 100 |
| 2.5 | 95 |
| 5 | 90 |
| 7.5 | 85 |
| 9 | 80 |
| 11 | 75 |
| 13 | 70 |

It is to be noted that the above tables are but exemplary and provided for purposes of concept. Depending on the desired concentration and/or amounts, correlated to the status of the BLB, a given amount of drug will be applied locally and systemically.

It is noted that different dosages could be applied for different BLB statuses. By way of example only and not by way of limitation, in an embodiment where the BLB is open and thus porous, it can be utilitarian to provide a higher systemic dosage than the local dosage relative to that which might otherwise be the case for those particular dosages, whereas, in an embodiment where the BLB is closed, it can be utilitarian to provide a lower systemic dosage than the local dosage, relative to that which would otherwise be the case for those particular dosages. The point is, that by managing or otherwise utilizing specific dosages at the local site and at the systemic site, alone or combined with management or otherwise evaluation of the status of the BLB, in an exemplary embodiment, the concentrations and/or the amounts can be managed in a manner that is more utilitarian than that which would be the case in the absence of practicing these teachings.

An exemplary embodiment can include a method where the BLB is maintained or otherwise is driven to be in a closed state when a drug is locally administered, and then the BLB is opened after a period of time where it is empirically or otherwise estimated or calculated that the therapeutic substance levels in the structure would have gone down, and then larger amounts of systemically administered drugs are provided and the gradient between the structure and the rest of the body is such that those drugs are drawn into the structure. In an exemplary embodiment, there is a method of forcing the BLB to stay closed and/or open for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47 or 48 hours or days or weeks. In an exemplary embodiment, the closure and/or the opening is accomplished, for example, via the utilization of a drug and/or a biotherapeutic substance, and/or other stimulation regimes as detailed herein. It is noted that the aforementioned closings and/or openings can correspond to a closure and/or opening that is at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 125, 150, 175, 200, 300, 400, 500, 600, 700, 800, 900, 1000, 1250, 1500, 1750, 2000, 2500, 3000, 3500, 4000, 4500 or 5000 or more percent greater (in the case of opening) or less (limited to 100% of course) in the case of closure, relative to that which would be the case without the intervention. Any device, system and/or method now or later developed that can open and/or close, fully or partially, the BLB, so that such can have utilitarian value can be utilized at least some exemplary embodiments.

In view of the above, it can be seen that in an exemplary embodiment, there is a method, comprising the action of administering a therapeutic substance to a person and managing a concentration and/or amount of the substance in a cochlea of the person by taking into account a blood labyrinth barrier of the person. In an exemplary embodiment, the action of managing the concentration and/or amount is executed by altering the blood labyrinth barrier. This can be done by opening and/or closing the barrier in any of the ways detailed herein and/or any other way that can have utilitarian value.

In some embodiments, the therapeutic substance is administered locally and systemically, and the management of the concentration and/or amount of the substance is executed by balancing the local amount and the systemic amount. The amount of substance administered locally and/or the amount of substance administered systemically is determined, in some embodiments, based on a state of the blood labyrinth barrier (e.g., open, closed, etc.). Again, such can be done to adjust the concentration gradient/obtain a concentration gradient of the substance between the inside of the cochlea and the outside of the cochlea, thereby managing the amount and/or concentration. In some embodiments, the amount of substance administered locally and the amount of substance administered systemically is determined to maintain or obtain the concentration and/or amount of the substance in the cochlea (or at a particular region of the cochlea or range of region(s), such as, for example, at locations corresponding to particular frequency places in the cochlea), wherein the amount provided locally is less than the maximum amount that could be efficaciously applied (i.e., the additional amount would be wasted). In an exemplary embodiment, the amount applied locally is 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90 or 95 percent of the amount that can be efficaciously applied. In some embodiments, the amount of substance amount provided systemically is less than the maximum amount that could be efficaciously applied (i.e., the additional amount would be wasted). In an exemplary embodiment, the amount applied locally is 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90 or 95 percent of the amount that can be efficaciously applied.

With respect to systemic administration, a compromised BLB can exists as a result of the injection of lipopolysaccharide (LPS). An exemplary embodiment includes systemic administration comprising an inflammatory component (such as LPS) and treatment that both target the inner ear. Such an exemplary embodiment also includes controlling or otherwise mitigating the systemic damage that results from executing such. In an exemplary embodiment, the methods can include systemically delivering molecules that are safe until they get to the ear or other target organ and then release the inflammatory payload (LPS or other). Accordingly, embodiments also include those molecules.

In an exemplary embodiment, there is an action of modifying the permeability of the round window and/or oval window a zap of some kind, such as an electrical shock or the like, and then delivering drug to the area. In an exemplary embodiment, an electrical current is applied to the round window and/or the oval window. In an exemplary embodiment mechanical stimulation is applied to the window(s), such as the utilization of a needle or a scratching device. In an exemplary embodiment, a chemical compound is applied to the permeability of the windows.

Consistent with the embodiment detailed above that utilize electrical current to implement at least some of the teachings detailed herein, such as to implement the trauma detailed above or otherwise elicit a foreign body response, in an exemplary embodiment, a cochlear implant electrode arrays utilized such that the Shannon limit is temporarily exceeded. This is the safe charge density for platinum electrodes (and in an exemplary embodiment, the electrodes utilized to provide the current are platinum electrodes). In an exemplary embodiment, this temporary exceeding of the Shannon limit can cause the trauma and/or open the BLB.

It is noted that the aforementioned Shannon limit can be linked to electrode size and or charge injection level. Accordingly, in an exemplary embodiment, there is a method of evaluating the current required to exceed the Shannon limit and/or the voltage requirements to exceed the Shannon limit by a certain percentage by taking into account electrode size and or electrode make up and/or the exposed area of the electrodes (e.g., portions that are not covered by silicone or other type of material) and controlling a conventional cochlear implant to exceed the Shannon limit by the aforementioned percentages. In an exemplary embodiment, the Shannon limit is exceeded by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 125, 150, 175, 200, 300, 400, 500, 600, 700, 800, 900, 1000, 1250, 1500, 1750, 2000, 2500, 3000, 3500, 4000, 4500 or 5000 percent (whatever is used to calculate the Shannon limit results in the increase) or more for more than or less than or equal to 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 125, 150, 175, 200, 300, 400, 500, 600, 700, 800, 900, 1000, 1250, 1500, 1750, 2000, 2500, 3000, 3500, 4000, 4500 or 5000 or more percent (or any value or range of values therebetween in 0.01 increments) the standard energizing time and/or average (mean or median or mode) for that given recipient of a given electrode utilized to evoke a hearing percept with the cochlear implant (e.g., the charge applied is 10 times the Shannon limit and the time that the charge is applied is twice the length of a standard pulse, where the standard pulse is 400 microseconds).

It is noted that in at least some embodiments, it is the heightened charge and not the dissolved platinum that invokes the response, or at least the main driver is the former and not the latter. In this regard, it is noted that the two are linked in some embodiments. The immediate impact of high current excursion can be damage to cells (along with some heat, protein denaturation and/or potentially generation of air bubbles). If one implements this over a reasonable period of time, platinum will also accumulate in the tissues, and such might also induce the trauma and/or open the BLB according to the teachings detailed herein.

In view of the above, there is an exemplary method that includes the action of managing the concentration and/or amount of a therapeutic substance in an organ by altering the blood labyrinth barrier by systemically delivering an inflammatory substance, such as LPS. In an exemplary embodiment, the action of managing the concentration and/or amount is executed by altering the blood labyrinth barrier by systemically delivering an inflammatory substance that has a deleterious effect on tissue of the recipient (e.g., LPS) when in a first state if delivered systemically in amounts to open the blood labyrinth barrier (e.g., without the noted molecules detailed above). In this embodiment, the inflammatory substance is delivered systemically in a second state that is different from the first state (in amounts that would be deleterious if in the first state), wherein the second state is a state in which there is less deleterious effect on tissue of the recipient relative to that of the first state (e.g., more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 75, 80, 85, 90, 91, 92, 93, 94, 95, 96, 97, 97, 98 or 99% or equal to 100% less deleterious), and the method further comprises transitioning the inflammatory substance from the second state to the first state when the substance is proximate the cochlea (or other target organ), thereby managing the concentration and/or amount of the substance in the cochlea (or other target organ). In an exemplary embodiment this can be done via a time-released system and/or via the application of stimulus, such as, for example, the application of electrical energy and/or the application of another substance that alters the body chemistry of the recipient temporarily (e.g., increases the salinity) which triggers the conversion from the second state to the first state and/or via the application of a stimulus that a state of the recipient, such as increasing and/or decreasing blood pressure of the recipients and/or inducing a temperature increase or decrease in the recipient.

In an exemplary embodiment, the action of managing the concentration and/or amount is executed by applying electrical stimulation from a cochlear implant electrode array located in a cochlea of the recipient such that platinum making up electrodes of the electrode array diffuse from the electrodes/released from the electrodes in amounts beyond that which occur during normal operation of the electrode array.

In an exemplary embodiment, the increase in platinum diffusion is 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 125, 150, 175, 200, 300, 400, 500, 600, 700, 800, 900, 1000, 1250, 1500, 1750, 2000, 2500, 3000, 3500, 4000, 4500 or 5000 or more percent above that which normally occurs.

It is further noted that any disclosure of a device and/or system detailed herein also corresponds to a disclosure of otherwise providing that device and/or system. Any disclosure herein of a method action corresponds to a device and/or system that is configured to execute that method action. Any disclosure herein of a device and/or system having functionality corresponds to a method of executing an action corresponding to that functionality. Any disclosure of a method of making a device and/or system corresponds to a device and/or system that results there from, and vice versa. It is further noted that any element of any embodiment detailed herein can be combined with any other element of any embodiment detailed herein unless stated so providing that the art enables such. It is also noted that in at least some exemplary embodiments, any one or more of the elements of the embodiments detailed herein can be explicitly excluded in an exemplary embodiment. That is, in at least some exemplary embodiments, there are embodiments that explicitly do not have one or more of the elements detailed herein. While various embodiments of the present invention have been described above, it should be understood that they have been presented by way of example only, and not limitation. It will be apparent to persons skilled in the relevant art that various changes in form and detail can be made therein without departing from the spirit and scope of the invention.

What is claimed is:

1. A method, comprising:
   monitoring a physical phenomenon inside a cochlea of a recipient; and
   managing a blood labyrinth barrier of the recipient based on the monitored physical phenomenon, wherein
   the action of managing the blood labyrinth barrier is executed by applying electrical stimulation from a cochlear implant electrode array located in the cochlea of the recipient.

2. The method of claim 1, wherein:
   the action of managing the blood labyrinth barrier includes inducing a change in a blood labyrinth barrier of the recipient based on the monitored physical phenomenon.

3. The method of claim 2, wherein:
   the change in the blood labyrinth barrier is an increase in the permeability thereof, and
   an amount and/or concentration of a substance in the cochlea is reduced due to the increase in the permeability relative to that which would be the case in the absence of the increase in the permeability.

4. The method of claim 3, wherein:
   the substance is a drug introduced into the body of the recipient at a location away from the cochlea and is a drug unrelated to a hearing ailment.

5. The method of claim 3, wherein:
   the substance is a drug introduced into the body of the recipient at a location inside the cochlea and/or proximate the cochlea.

6. The method of claim 2, wherein:
   the change in the blood labyrinth barrier is an increase in the permeability thereof; and
   an amount and/or concentration of substance in the cochlea is increased due to the increase in the permeability relative to that which would be the case in the absence of the increase in the permeability.

7. The method of claim 6, wherein:
   the substance is a drug introduced into the body of the recipient at a location away from the cochlea and is a drug related to treatment of the hearing system of the recipient.

8. The method of claim 2, wherein:
the action of inducing a change in a blood labyrinth barrier of the recipient is executed also via the injection of an inflammatory compound to a scala tympani of a cochlea.

9. The method of claim 1, wherein:
the physical phenomenon is a phenomenon correlated to ototoxicity.

10. The method of claim 1, wherein:
the action of managing the blood labyrinth barrier includes purposely altering the blood labyrinth barrier, wherein the action of altering the blood labyrinth barrier controllably increases and/or decreases a rate of transfer of a therapeutic substance from inside the cochlea to outside the cochlea and thereby changes a concentration and/or amount of the therapeutic substance inside the cochlea.

11. A method, comprising:
administering a therapeutic substance to a person; and
inflicting trauma in or proximate an anatomical structure of the person, thereby adjusting a concentration and/or amount of the therapeutic substance in the anatomical structure relative to that which would be the case in the absence of the trauma, wherein
the trauma is executed by applying electrical stimulation from an electrode located in the person.

12. The method of claim 11, wherein:
the adjustment is a reduction in an amount and/or concentration of therapeutic substance in the anatomical structure relative to that which would be the case in the absence of the trauma.

13. The method of claim 11, wherein:
the adjustment is an increase in the amount and/or concentration of therapeutic substance in the anatomical structure relative to that which would be the case in the absence of the trauma.

14. The method of claim 11, wherein:
the anatomical structure is a cochlea.

15. The method of claim 11, wherein:
the anatomical structure is one of a kidney or an eye.

16. The method of claim 11, wherein:
the anatomical structure is a cochlea;
the person is a recipient of a cochlear implant that includes an electrode array inserted into the cochlea that includes the electrode.

17. The method of claim 16, further comprising:
automatically proffering, via the cochlear implant and/or a support device therefor, at least one of a reminder or an inquiry to the person respectively instructing the person to execute the action of administering the therapeutic substance to the person;
receiving, in response to the automatic proffering, feedback from the person indicating that the person has administered himself/herself the therapeutic substance and thus has executed the action of administering a therapeutic substance to the person; and
based on the received feedback, inflicting the trauma using the cochlear implant.

18. The method of claim 11, wherein:
the action of inflicting trauma is executed also by applying an irritant to the structure of the person.

19. The method of claim 18, wherein:
the irritant is at least one of a chemical based irritant or a mechanical based irritant.

20. The method of claim 18, wherein:
the irritant is applied to a structure of the cochlea and/or of the middle ear; and
the action of administering the therapeutic substance to the person is executed by administering the substance at a location remote from the structure.

21. The method of claim 11, wherein:
the anatomical structure is a cochlea;
the person is a recipient of a cochlear implant that includes an electrode array inserted into the cochlea; and
the cochlear implant inflicts the trauma by exceeding a Shannon limit of electrodes of the electrode array.

22. A method, comprising:
administering a therapeutic substance to a person; and
managing a concentration and/or amount of the substance in a cochlea of the person by taking into account a blood labyrinth barrier of the person, wherein
the action of managing the concentration and/or amount is executed by applying electrical stimulation from a cochlear implant electrode array located in a cochlea of the recipient.

23. The method of claim 22, wherein:
the action of managing the concentration and/or amount is executed by altering the blood labyrinth barrier.

24. The method of claim 22, wherein:
the therapeutic substance is administered locally and systemically; and
the management of the concentration and/or amount of the substance is executed by balancing the local amount and the systemic amount.

25. The method of claim 22, wherein:
the therapeutic substance is administered locally and systemically; and
the amount of substance administered locally and the amount of substance administered systemically is determined based on a state of the blood labyrinth barrier.

26. The method of claim 22, wherein:
the therapeutic substance is administered locally and systemically; and
the amount of substance administered locally and the amount of substance administered systemically is determined so as to obtain a concentration gradient of the substance between the inside of the cochlea and the outside of the cochlea, thereby managing the amount and/or concentration.

27. The method of claim 22, wherein:
the therapeutic substance is administered locally and systemically; and
the amount of substance administered locally and the amount of substance administered systemically is determined to maintain the concentration and/or amount of the substance in the cochlea, wherein the amount provided locally is less than the maximum amount that could be efficaciously applied.

28. The method of claim 22, wherein:
the action of managing the concentration and/or amount is executed also by applying the electrical stimulation from the cochlear implant electrode array located in the cochlea of the recipient such that platinum making up electrodes of the electrode array diffuse from the electrodes in amounts beyond that which occur during normal operation of the electrode array to evoke a hearing percept.

29. The method of claim 22, wherein:
the action of managing the concentration and/or amount is executed by applying the electrical stimulation from the cochlear implant electrode array located in the cochlea of the recipient such that a Shannon limit is intentionally exceeded.

30. The method of claim 22, wherein:
the action of managing the concentration and/or amount is executed also by altering the blood labyrinth barrier by systemically delivering an inflammatory substance.

31. The method of claim 22, wherein:
the action of managing the concentration and/or amount is executed also by altering the blood labyrinth barrier by systemically delivering an inflammatory substance that has a deleterious effect on tissue of the recipient when in a first state if delivered systemically in amounts to open the blood labyrinth barrier;
the inflammatory substance is delivered systemically in a second state that is different from the first state, wherein the second state is a state in which there is less deleterious effect on tissue of the recipient relative to that of the first state; and
the method further comprises transitioning the inflammatory substance from the second state to the first state when the substance is proximate the cochlea, thereby managing the concentration and/or amount of the substance in the cochlea.

* * * * *